(12) United States Patent
Xie et al.

(10) Patent No.: US 11,642,520 B2
(45) Date of Patent: May 9, 2023

(54) ELECTRONIC SKIN REJUVENATING DEVICE AND METHODS OF USE

(71) Applicant: UVVU, INC., Los Angeles, CA (US)

(72) Inventors: Zuowo Xie, Shenzhen (CN); Sijia Chen, Shenzhen (CN); Shengbiao Lin, Shenzhen (CN); Andrew Silberstein, Venice, CA (US)

(73) Assignee: UVVU, Inc., Los Angeles, CA (US)

( * ) Notice: Subject to any disclaimer, the term of this patent is extended or adjusted under 35 U.S.C. 154(b) by 0 days.

(21) Appl. No.: 17/856,894

(22) Filed: Jul. 1, 2022

(65) Prior Publication Data

US 2022/0331585 A1 Oct. 20, 2022

Related U.S. Application Data

(63) Continuation of application No. PCT/US2022/020170, filed on Mar. 14, 2022.

(60) Provisional application No. 63/160,647, filed on Mar. 12, 2021.

(51) Int. Cl.
*A61N 5/06* (2006.01)
*A61H 23/02* (2006.01)
*A61N 1/32* (2006.01)
*A61N 1/36* (2006.01)
*A61F 7/00* (2006.01)

(52) U.S. Cl.
CPC ............... *A61N 1/328* (2013.01); *A61F 7/00* (2013.01); *A61H 23/02* (2013.01); *A61N 1/36034* (2017.08); *A61N 5/0616* (2013.01); *A61F 2007/0087* (2013.01); *A61H 2201/0153* (2013.01); *A61H 2201/10* (2013.01); *A61N 2005/0644* (2013.01); *A61N 2005/0663* (2013.01)

(58) Field of Classification Search
CPC .................. A61N 5/0616; A61N 1/328; A61N 2005/0644; A61N 2005/0652; A61N 2005/0659; A61H 23/02; A61H 2201/0153; A61H 2201/10
See application file for complete search history.

(56) References Cited

U.S. PATENT DOCUMENTS

| 2,490,074 | A | 12/1949 | Marty | |
|---|---|---|---|---|
| 6,181,974 | B1 * | 1/2001 | Springer, Jr. | A61N 1/0452 607/140 |
| 6,187,029 | B1 * | 2/2001 | Shapiro | A61N 5/0616 607/91 |
| 6,443,915 | B1 * | 9/2002 | Hwang | A61N 1/32 601/72 |

(Continued)

FOREIGN PATENT DOCUMENTS

| CN | 205672195 U | 11/2016 |
|---|---|---|
| CN | 211301796 U | 8/2020 |

(Continued)

OTHER PUBLICATIONS

International Searching Authority/USPTO, International Search Report and Written Opinion issued in corresponding application PCTUS2022020170 dated Jun. 7, 2022 (11 pages).

*Primary Examiner* — Justine R Yu
*Assistant Examiner* — Christopher E Miller
(74) *Attorney, Agent, or Firm* — J. Peter Paredes; Amin Talati Wasserman LLP

(57) ABSTRACT

Provided herein are systems, methods and apparatuses for an Electronic skin rejuvenating device.

19 Claims, 21 Drawing Sheets

(56) References Cited

U.S. PATENT DOCUMENTS

| | | | | |
|---|---|---|---|---|
| 7,503,927 | B1* | 3/2009 | Vetanze | A61N 1/322 607/152 |
| 8,983,596 | B2* | 3/2015 | Mantle | A61N 1/32 607/46 |
| 9,585,687 | B2 | 3/2017 | Tenenbaum et al. | |
| 2003/0199946 | A1* | 10/2003 | Gutwein | A61N 5/0616 607/88 |
| 2006/0287696 | A1* | 12/2006 | Wright | A61N 5/0613 607/96 |
| 2007/0185553 | A1* | 8/2007 | Kennedy | A61N 5/0616 607/100 |
| 2009/0048557 | A1* | 2/2009 | Yeshurun | A61B 18/203 604/20 |
| 2009/0088824 | A1* | 4/2009 | Baird | A61N 5/0617 607/90 |
| 2009/0093864 | A1* | 4/2009 | Anderson | A61B 18/1477 607/99 |
| 2010/0121419 | A1* | 5/2010 | Douglas | A61N 5/0616 607/90 |
| 2010/0292746 | A1* | 11/2010 | Gorham | A61B 18/04 607/3 |
| 2013/0046212 | A1* | 2/2013 | Nichols | A61N 1/00 601/18 |
| 2014/0128780 | A1 | 5/2014 | Kennedy et al. | |
| 2016/0331308 | A1* | 11/2016 | Zhou | A61M 35/003 |
| 2018/0133469 | A1* | 5/2018 | Palero | A61N 1/06 |
| 2019/0183562 | A1* | 6/2019 | Widgerow | A61B 18/1206 |
| 2020/0085015 | A1* | 3/2020 | Yoo | H05K 1/14 |
| 2020/0154874 | A1* | 5/2020 | Tammabattula | A46B 13/023 |
| 2020/0253811 | A1 | 8/2020 | Alexander | |
| 2020/0316800 | A1* | 10/2020 | Beerwerth | B26B 19/46 |
| 2022/0134094 | A1* | 5/2022 | Kim | A61N 1/327 601/20 |
| 2022/0369792 | A1* | 11/2022 | Kim | A61N 5/067 |

FOREIGN PATENT DOCUMENTS

| | | |
|---|---|---|
| CN | 113648197 A | 11/2021 |
| CN | 215608807 U | 1/2022 |
| CN | 215649650 U | 1/2022 |
| CN | 217244779 U | 8/2022 |
| CN | 217246265 U | 8/2022 |

\* cited by examiner

FIG. 16
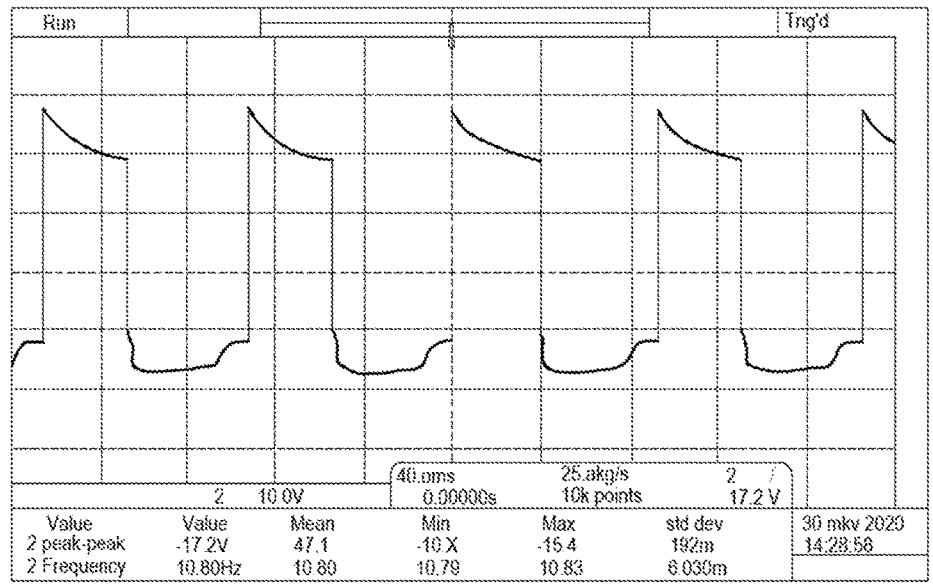
Before      Week 2      Week 3
FIG. 17A      FIG. 17B      FIG. 17C

ELECTRONIC SKIN REJUVENATING DEVICE AND METHODS OF USE

CROSS-REFERENCE TO RELATED APPLICATIONS

The present application claims priority to PCT application serial no. PCT/US2022/020170, filed Mar. 14, 2022, which claims priority to U.S. provisional application Ser. No. 63/160,647, filed Mar. 12, 2021, all herein incorporated by reference in their entities.

BACKGROUND

The invention generally relates to beauty devices that is used to rejuvenate the skin, including the skin of the face, body, scalp, periorbital, and neck.

The NuFace Mini device only includes microcurrent therapy, while LightStim for Wrinkles only includes red light therapy and also requires to be plugged in to an outlet during use, whereas ours is rechargeable and portable.

The disadvantages of using these prior products is they offer fewer technologies and functions, only helping improve certain elements of the skin's appearance. For instance, NuFace Mini is shown to lift and tone skin because of its microcurrent, but does not play a role in reducing the appearance of blemishes or wrinkles. LightStim for Wrinkles helps reduce the appearance of wrinkles, blemishes, and scars, but does not lift or tone the skin.

The present application attempts to solve these problems, as well as others.

SUMMARY OF THE INVENTION

Provided herein are systems, methods and apparatuses for an Electronic skin rejuvenating device to treat facial and skin conditions.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

BRIEF DESCRIPTION OF THE DRAWINGS

In the accompanying figures, like elements are identified by like reference numerals among the several preferred embodiments of the present invention.

FIG. 16 is a graph of the Tektronix Oscilloscope measurement of the Electronic skin rejuvenating device.

FIGS. 17A-17C are photographs of a subject before Electronic skin rejuvenating device treatment, showing the subject had wrinkles and damaged skin as shown in FIG. 17A; and after treatment of the skin and face with the Electronic skin rejuvenating device apparatus, the subject skin and face improved, as shown in FIGS. 17B-17C, after 2 weeks and 3 weeks of treatment by the Electronic skin rejuvenating device apparatus, respectively.

FIG. 18A is a front view of the Electronic skin rejuvenating device apparatus; FIG. 18B is a front view of the Electronic skin rejuvenating device with the head portion rotated 90 degrees; and FIG. 18C is a front view of the Electronic skin rejuvenating device apparatus with the heating system turned on.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

The term "synergistic" or "synergy" as used herein is refers to the phenomenon wherein the cumulative biological and physiological effect of two or more methods of skin therapy when used in combination is higher than the sum of the effect of each of them tested individually.

Figure 1A:
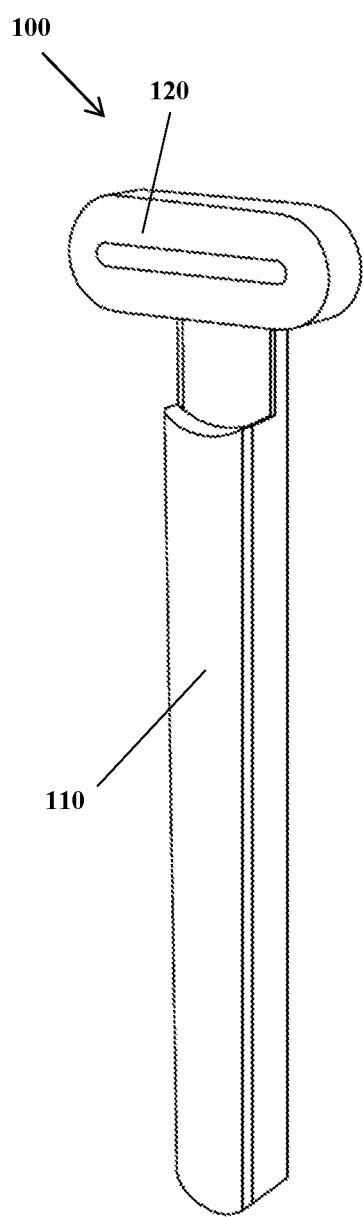
FIG. 1A is a perspective view of the Electronic skin rejuvenating device with the head portion rotated with respect to the handle portion.
Figure 1B:
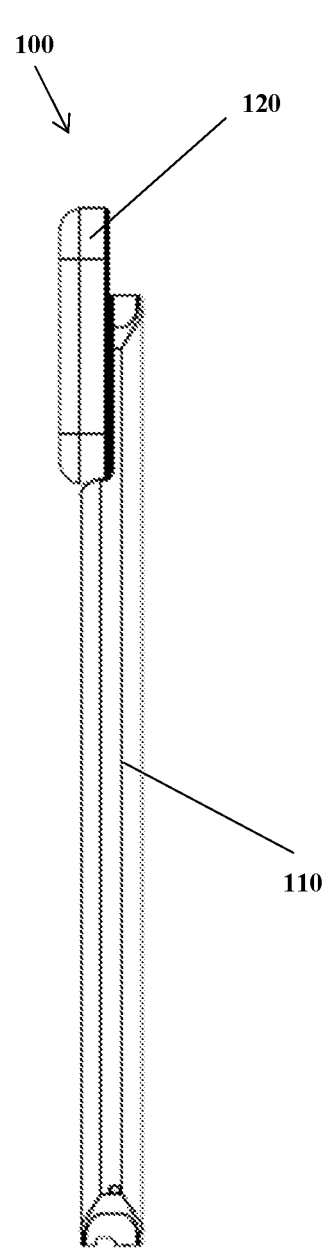
FIG. 1B is a side view of the Electronic skin rejuvenating device with the head portion parallel with respect to the handle portion.
Figure 1C:
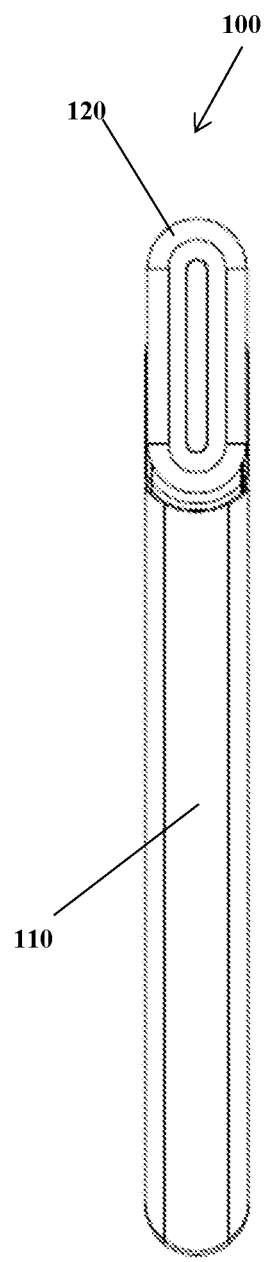
FIG. 1C is a front view of the Electronic skin rejuvenating device with the head portion parallel with respect to the handle portion.
Figure 2A:
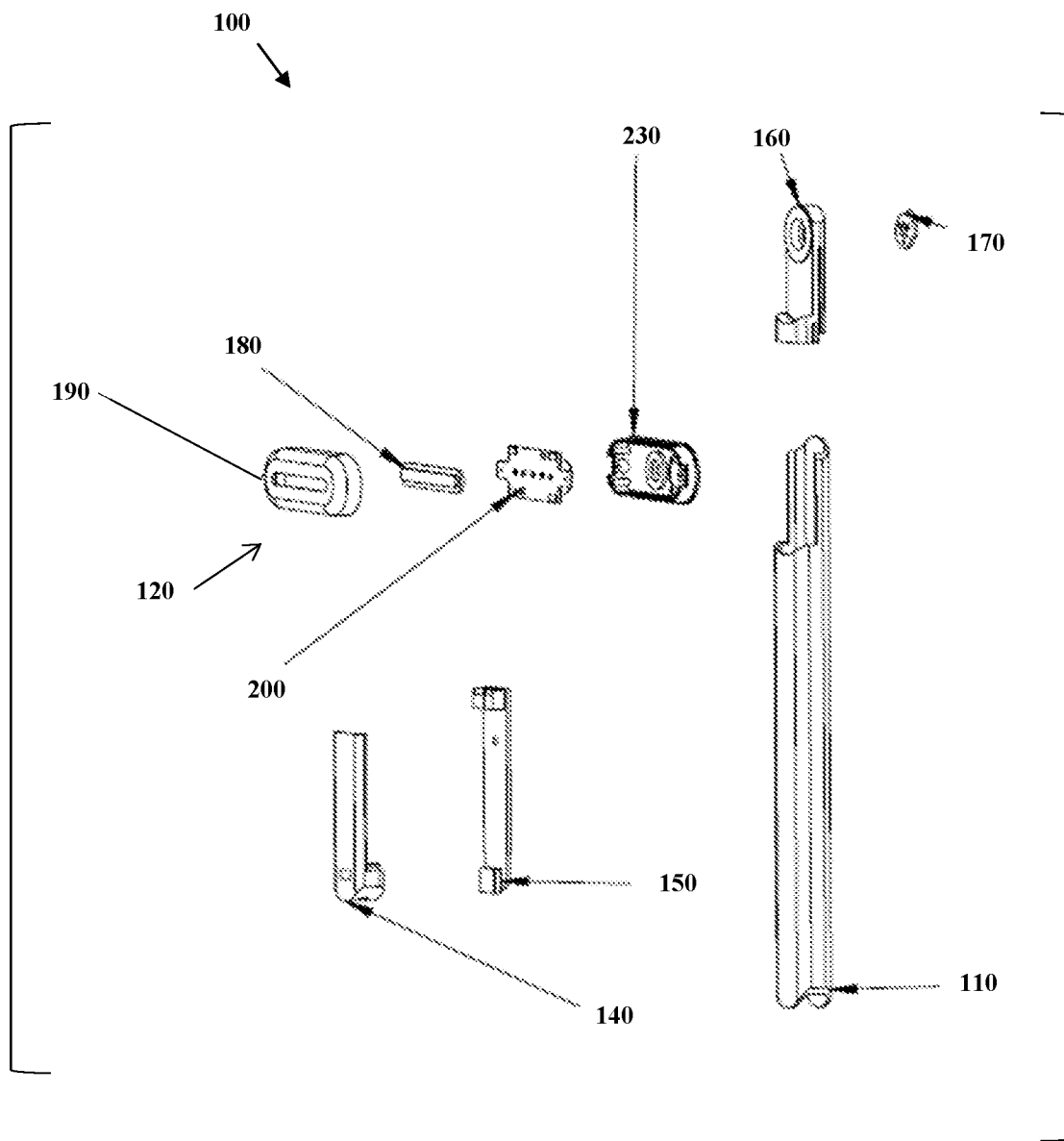
FIG. 2A is an exploded view of the Electronic skin rejuvenating device with the head portion and the handle portion.
Figure 2B:
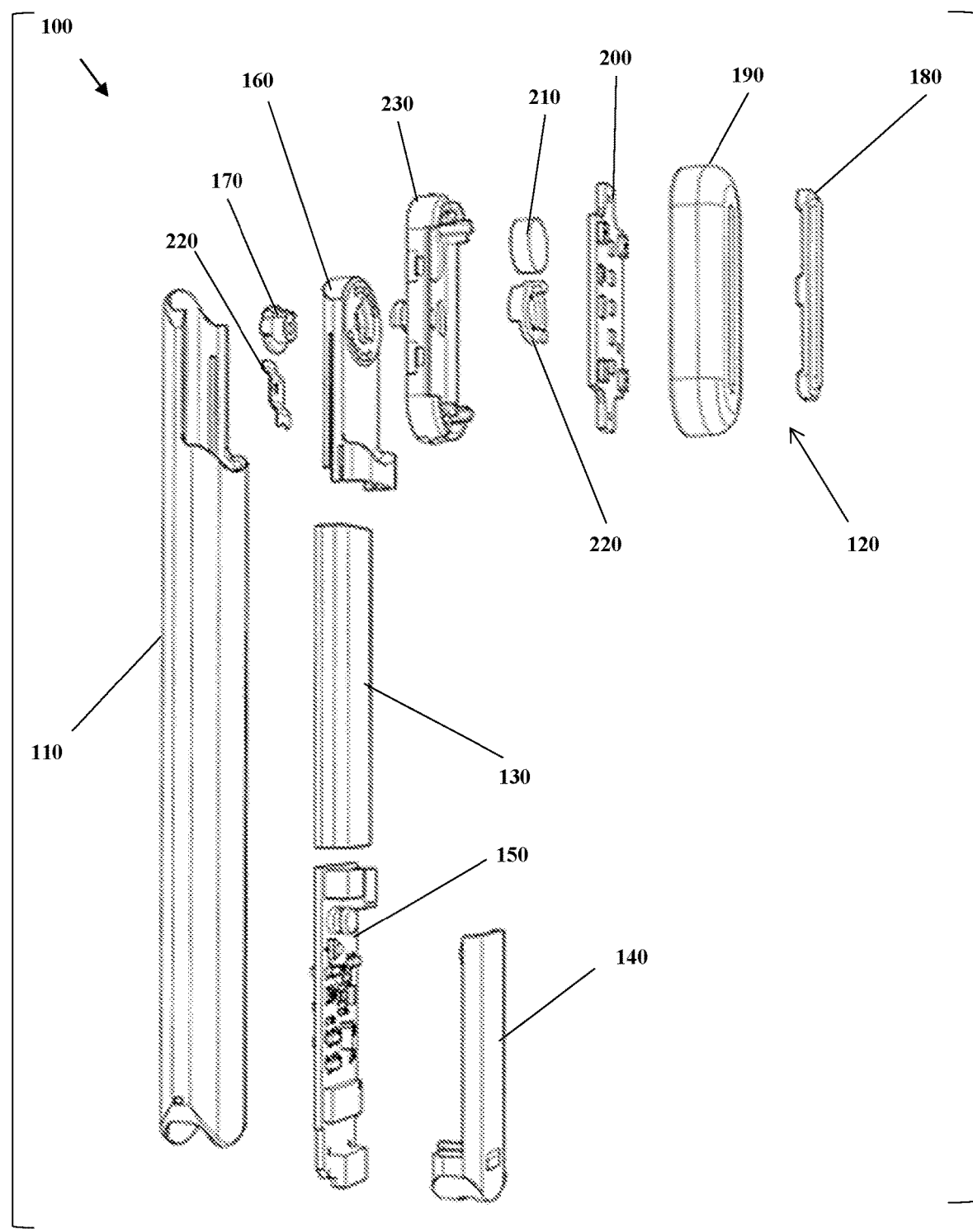
FIG. 2B is an exploded view of the Electronic skin rejuvenating device with the head portion and the handle portion, according one embodiment.

Generally speaking, the Electronic skin rejuvenating device 100 rejuvenate the skin of the face and neck comprising a handle portion 110 and a head portion 120, wherein the head portion 120 is rotatable about an axis or alternatively the head portion 120 is fixed about the axis with respect to the handle portion, as shown in FIGS. 1A-1C. The Electronic skin rejuvenating device treats skin conditions selected from the group consisting of: wrinkles, fine lines, acne, Fade blemishes, acne, breakouts, puffiness, and dark circles. The handle portion 110 comprises a bottom housing 140, a handle circuit board 150, a top mount 160, and a back ring 170 as shown in FIG. 2A. The head portion 120 comprises a cover 180, a head cover 190, a head circuit board 200, a head housing 230, as shown in FIG. 2A. In an alternative embodiment, the handle portion 110 comprises a power source 130, a bottom housing 140, a handle circuit board 150, a top mount 160, and a back ring 170, as shown in FIG. 2B. In an alternative embodiment, the head portion 120 comprises a cover 180, a head cover 190, a head circuit board 200, a head motor 210, a rotatable coupler 220, a head housing 230, as shown in FIG. 2B.

Figure 3A:
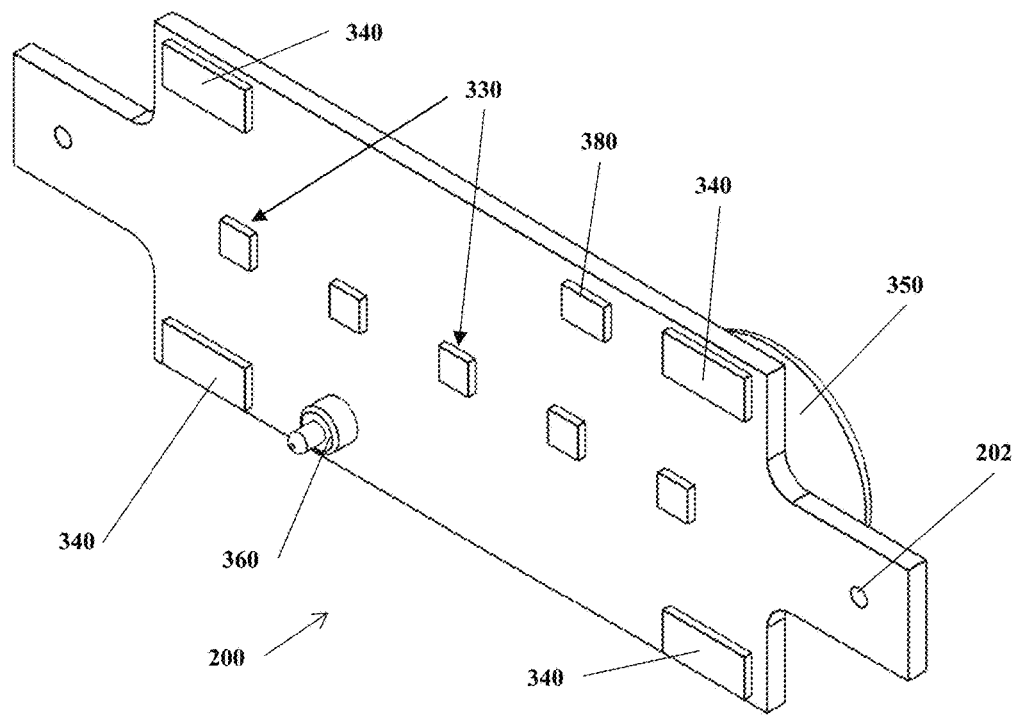
FIG. 3A is a perspective top view of the head circuit board of the Electronic skin rejuvenating device.
Figure 3B:
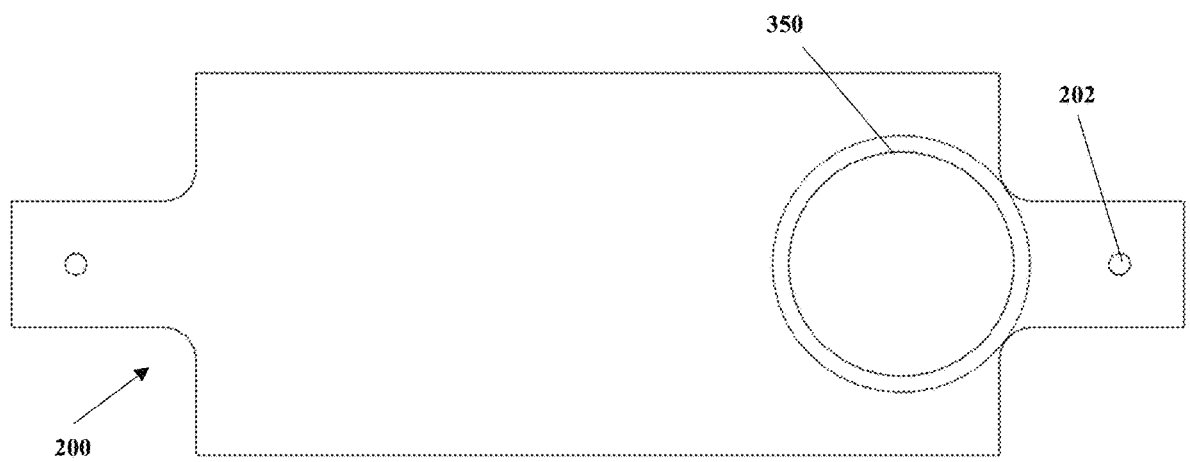
FIG. 3B is a perspective back view of the head circuit board.

The head circuit board 200 comprises a light therapy system 330, a warming system 340, a vibrating massage system 350, and a microcurrent therapy system 360, as shown in FIGS. 3A-3B. The Electronic skin rejuvenating device is a small handheld tool powered by a power source 130, as shown in FIG. 2B. The power source 130 is operably coupled with the light therapy system 330, the warming system 340, the vibrating massage system 350, and the microcurrent therapy system 360. In one embodiment, the microcurrent therapy system 360 is a galvanic current system. Galvanic currents are used for facial muscles through the skin and applies mild electric currents that consist of positive and negative electrodes to stimulate the local muscles. The galvanic current or the microcurrent may be AC, DC, or alternate between AC and DC voltage. The outcome of a galvanic current is maintaining the muscle physiology or muscle tone, according to one embodiment. The power source 130 is a battery according to one embodiment, and rechargeable using a charging cable, according to one embodiment. The power source includes a power and voltage to supply the microcurrent, heating, vibrating, and light system, and may be directed plugged into a power supply, such as a power outlet, portable charger, and the like. The light therapy system 330 comprises a plurality of light emitting sources that emit a light therapy or a therapeutic light, wherein the therapeutic light comprises either red light between about 630 nm to about 670 nm or blue light between about 410 nm to about 465 nm. Alternatively, the light therapy system emits the light therapy in both the red light energy and the blue light energy, which would produce a purple light energy. In one embodiment, the red light energy includes a wavelength at 630 nm, 650 nm, and 660 nm; while the blue light energy includes a wavelength at 415 nm, 440 nm and 465 nm In one embodiment, the plurality of light emitting sources are light-emitting diodes (LED). The warming system 340 warms the skin to between about 93 and about 110 degrees Fahrenheit and the vibrating massage system comprises a motor to vibrate the head portion against the skin. The head portion 120 of the device comprises a head circuit board 200 that supports the plurality of light sources 330, the microcurrent therapy system 360, the warming system 340, a vibrating massage system 350. The Electronic skin rejuvenating device comprises an electromechanical configuration synergistically employing heat, light, vibration and Micro-current Electrical Neuromuscular Stimulation methods and treatments, as exemplified by the Examples below.

The Electronic skin rejuvenating device effectively treats eye and facial skin problems. The warming system effectively relieves eye fatigue and promotes blood circulation. By applying a treatment adherence plan, the warming system treats eye problems such as dark circles, eye bags, and edema. In one embodiment, the warming system can promote the absorption of eye mask and eye cream. In one embodiment, the light system uses a 660 nanometer (nm) red light or a 415 nm blue light to produce photochemical effects on tissue and skin and has important biological and therapeutic effects. The light system includes a power output between about 2.06 mw/cm$^2$ and about 100.00 mw/cm$^2$. In one embodiment, the light system includes about 7 red LEDs and about 7 blue LEDs; alternatively between about 2 red LEDs and 10 red LEDS, and between about 2 blue LEDs and 10 blue LEDs. The micro-current system treats and stimulates the skin and accelerates skin metabolism. The vibrating massage system may be used with eye cream and provide an increased absorption of eye cream. The warming system also helps topical products (serums, creams, and moisturizers) penetrate into at least 0.1 μm into the skin, alternatively, penetrate deeply into the skin, which leads to an increase between about 100% and 5000% in the absorption of topical products. In one embodiment, the 90° rotation of the head portion with respect to the handle portion adapt to different parts of the skin and body, such as the eye area and the lip area, as well as the entire face and neck skin. In one embodiment, the device includes a push on/off button or touch sensors for on/off control of the device. In another embodiment, the Electronic skin rejuvenating device includes a smart touch switch comprising electronic smart induction technology, which starts all the systems with a touch or pressure or smart power saving. When holding the handle portion, the head portion touches the skin to start working all systems, and the Electronic skin rejuvenating device stops when the head portion is removed from the skin, according to one embodiment.

In one embodiment, the handle portion does not include any buttons to operate; the head portion comprises a touch activation sensor 380 that turns the Electronic skin rejuvenating device on when the touch activation sensor 380 detects or contacts hydrated skin with the head portion. The Electronic skin rejuvenating device uses an impedance activation scheme. When held by the user, the device senses the impedance between the head and the body of the wand and activates the unit if the design detects an impedance of about 13 megohms or less.

As shown in FIGS. 3A-3B, the head circuit board 200 includes a motor 350 that vibrates at a rate between about 300 and about 30000 microvibrations per minute, alternatively, between about 1000 and about 20000 microvibrations per minute; alternatively, between about 10000 and 17000 microvibrations per minute; alternatively, between about 15000 and 16000 microvibrations per minute. Microvibrations may include an amplitude between about 100 microns to about 10000 microns and a plurality of patterns selected from sinosoidal. As used herein, the term "microvibration" refers to an agile reciprocating linear motion centered on an equilibrium position, or a symmetric or asymmetrical agile circular motion about an axis, and a physical "vibration" in the field of physics. Reference shall be made to any other suitable movement consistent with a known meaning. When the device is placed in contact with the skin, any microvibration will move the skin or tissue in any direction more than 100 microns. Vibration helps promote blood circulation and increase lymphatic flow, which temporarily reduces the appearance of dull skin. It can help visibly reduce the appearance of dark circles and redness. Microvibrations can activate metabolism and reduce fibrosis.

The head portion 120 includes a spring loaded pogo pin 360 that presses on the inside of front cover 190 of the head portion 120 to transfer the other pole of a microcurrent generator to the head portion of the Electronic skin rejuvenating device. The micro current is delivered to the head portion of the device using the body of the handle portion 110 as the return connection. The micro current flows through the users' hand and body and the circuit is completed at the interface of the Electronic skin rejuvenating device's head portion and the skin it is applied to. In one embodiment, the micro current includes a global or whole body effect when the circuit is completed.

Figure 4A:
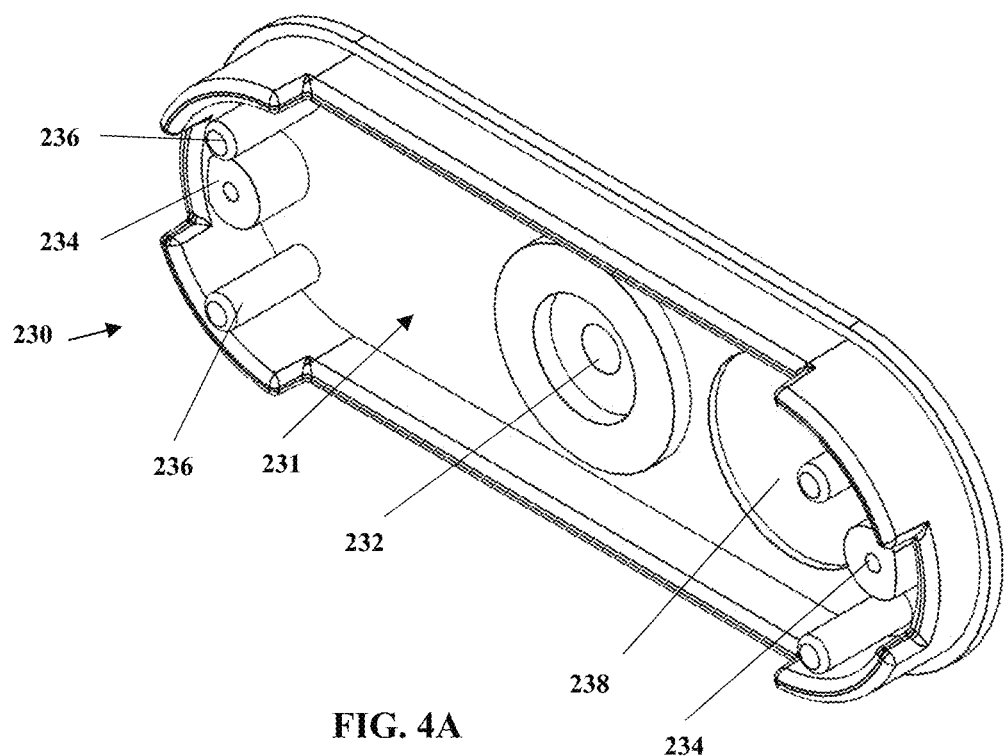
FIG. 4A is a perspective back view of the head housing.
Figure 4B:
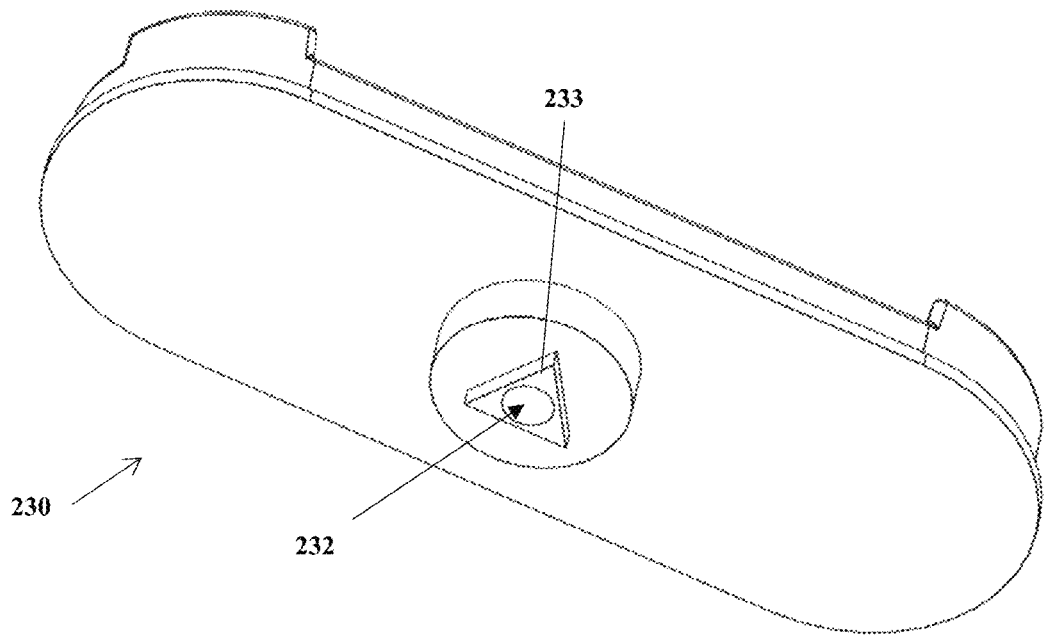
FIG. 4B is a perspective front view of the top head housing.

As shown in FIGS. 4A-4B, the head housing 230 comprises a mounted seat 231 for the head circuit board 200 to be secured therewithin. The head housing 230 comprises at least two seated pins 234 to secure the head circuit board 200, whereby the seated pins 234 coaxially couple through the at least two holes 202 on the exterior flanges of the head circuit board 200. The head housing 230 comprises a central lumen portion 232, whereby the head housing 230 is rotatable about a central axis of the central lumen portion. In one embodiment, the central lumen portion 232 includes a triangular seat 233 on the exterior surface of the head housing 230. The triangular seat 233 allows the head housing 230 to rotate to a fixed position, such that the head housing 230 rotates to a right angle with respect to the handle portion. The head housing 230 comprises at least four seated columns 236 by which the head housing 230 is secured to the front cover.

Figure 5A:
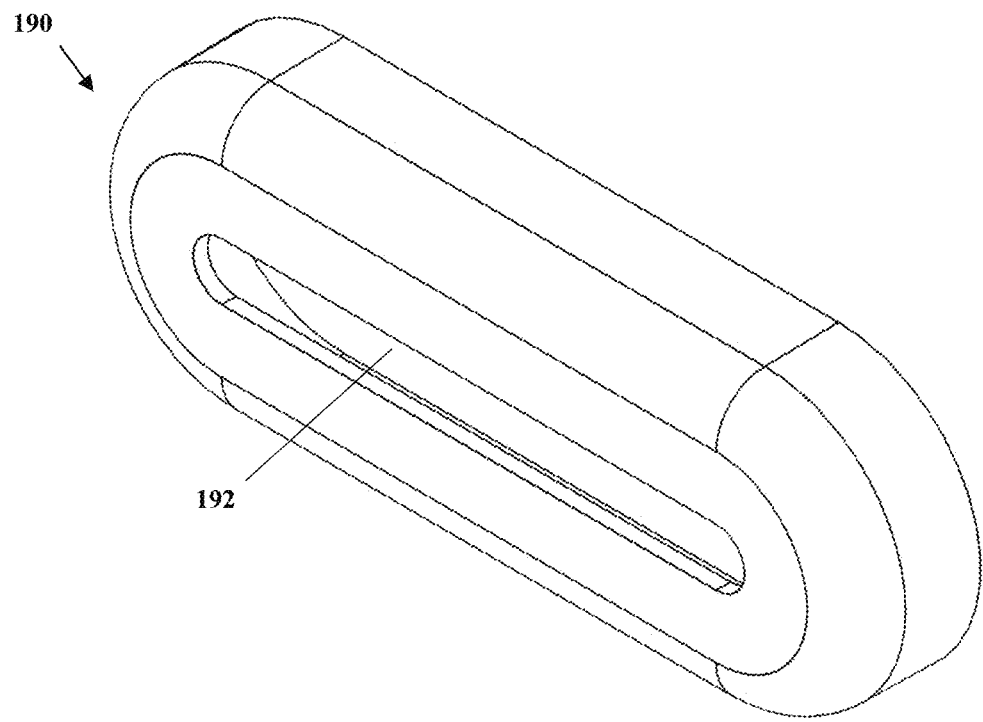
FIG. 5A is a perspective front view of the head cover.
Figure 5B:
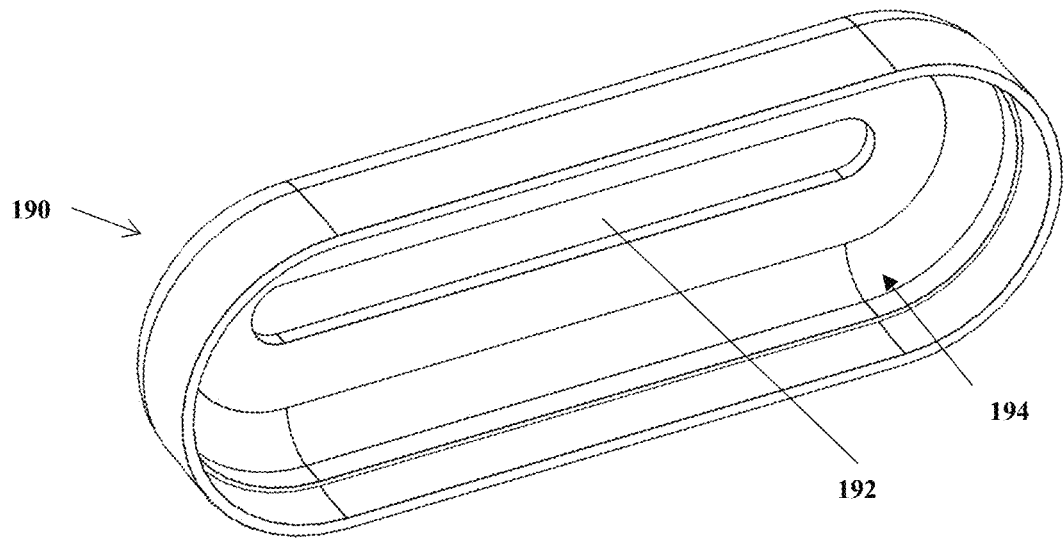
FIG. 5B is a perspective back view of the head cover.

As shown in FIG. 5A-5B, the front cover 190 includes generally curvilinear configuration shaped to fit over the head housing 230. The front cover 190 comprises a central window portion 192 sized to permit the light system from the head housing 230 to transmit optical energy through the window 192. In one embodiment, the cover 180 fits over the central window portion 192. The front cover 190 comprises a cover lumen portion 194 that fits over the exterior and circumference of the head housing 230. The four seated columns 236 may be sealed or joined to the cover lumen portion 194 by a solder, weld, or other sealing means. The material of the front cover 190 permits the micro current system to transmit microcurrent there through to the user's skin. The cover 180 may include a material to separate the LEDs from the surface of the skin, or the cover 180 may include a lens as to focus the LED energy onto the skin. In one embodiment, the lens includes a thickness and a tint to permit the red light and blue light to traverse there through without affecting the light energy power, intensity, or wavelength. The lens is transparent and the LEDs are placed as close as possible behind this lens. The tint of the lens may be varied according to the LED light energy being used. The cover may include a glass or polymer material.

Figure 6A:
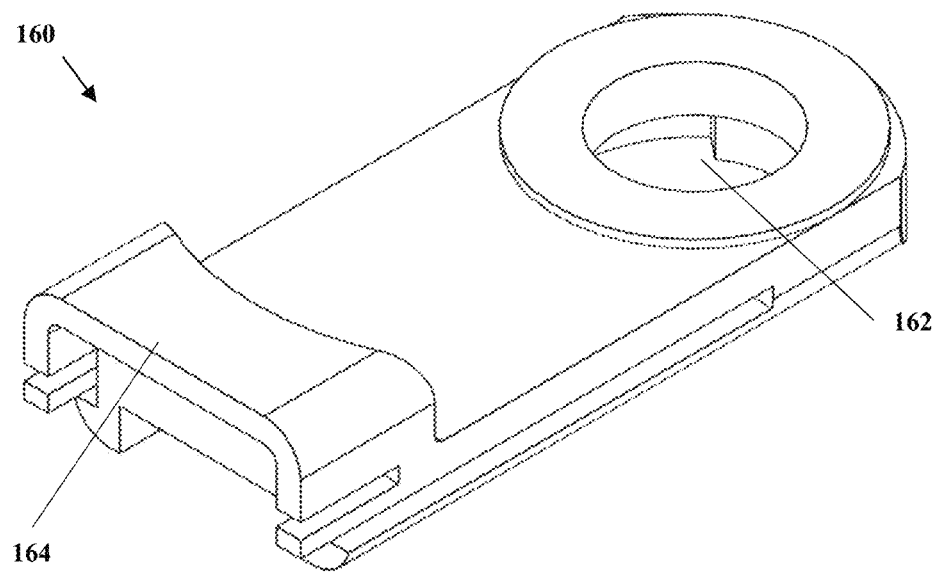
FIG. 6A is perspective front view of the top mount.
Figure 6B:
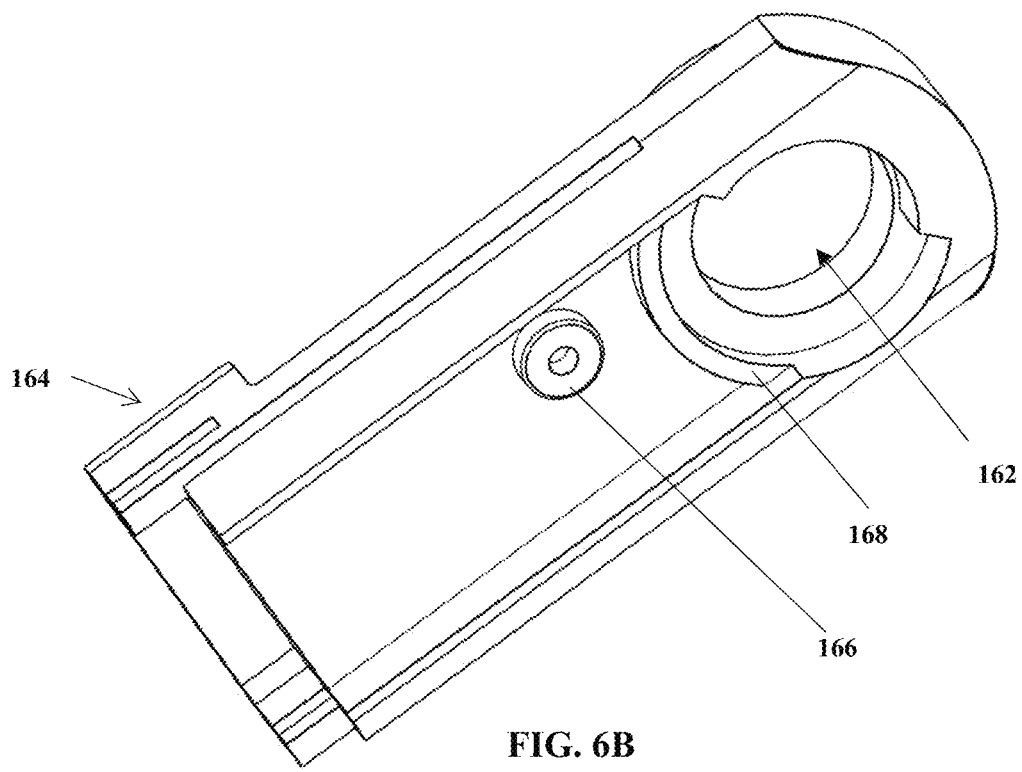
FIG. 6B is a perspective back view of the top mount.

As shown in FIGS. 6A-6B, the top mount 160 includes a top circular portion 162 and a bottom slotted portion 164. The bottom slotted portion 164 is secured with the handle portion 110. The top mount 160 further comprises a circular seat 166 on the back portion to further secure the top mount 160 to the handle portion 110. The top circular portion 162 rotatably couples with the head housing 230 and the central lumen portion 232 and the triangular seat 233. The head housing 230 is secured and rotatably coupled to the top mount 160 by way of the back ring 170. The top circular portion 162 includes a slotted circular seat 168 in which to secure the back ring 170.

Figure 7:
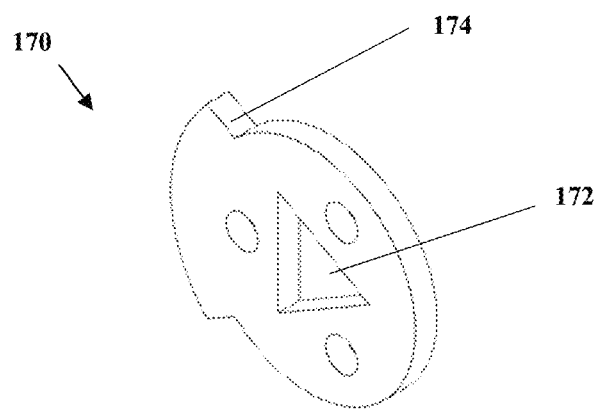
FIG. 7 is a perspective front view of the back ring.

As shown in FIG. 7, the back ring 170 include a central triangular portion 172 that operably couples with the head housing 230 and the triangular seat 233. The back ring 170 includes an outer stop portion 174, which stops the rotation of the head housing 230 to be at a right angle with respect to the handle portion 110.

Figure 8:
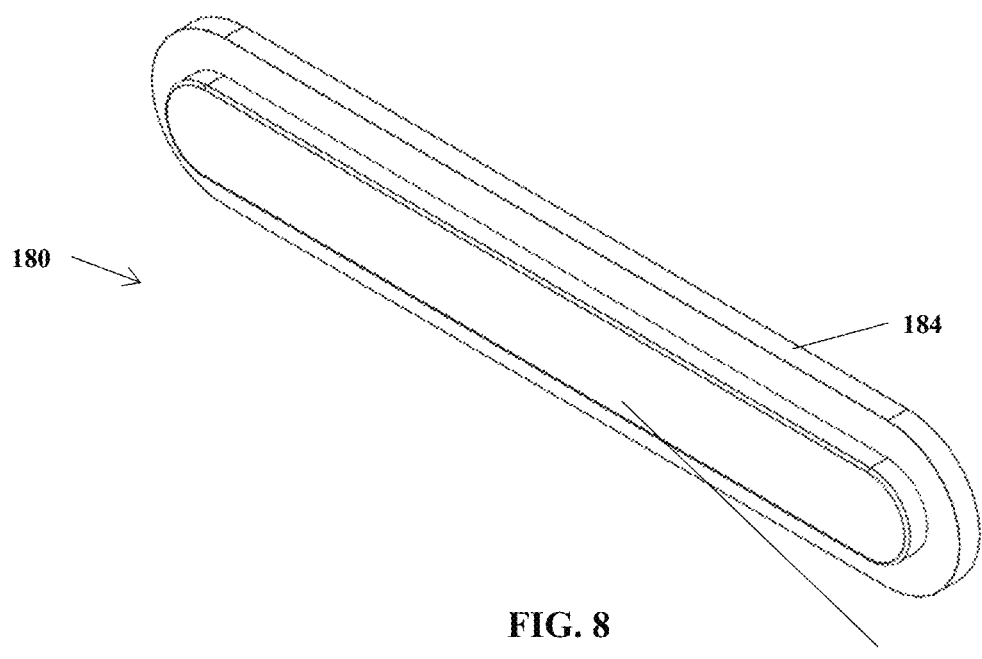
FIG. 8 is a perspective back view of the cover.

As shown in FIG. 8, the cover 180 comprises a seated portion 182 to fit within over the central window portion 192 of the head housing 190. The cover 180 may be a clear and transparent cover.

Figure 9:
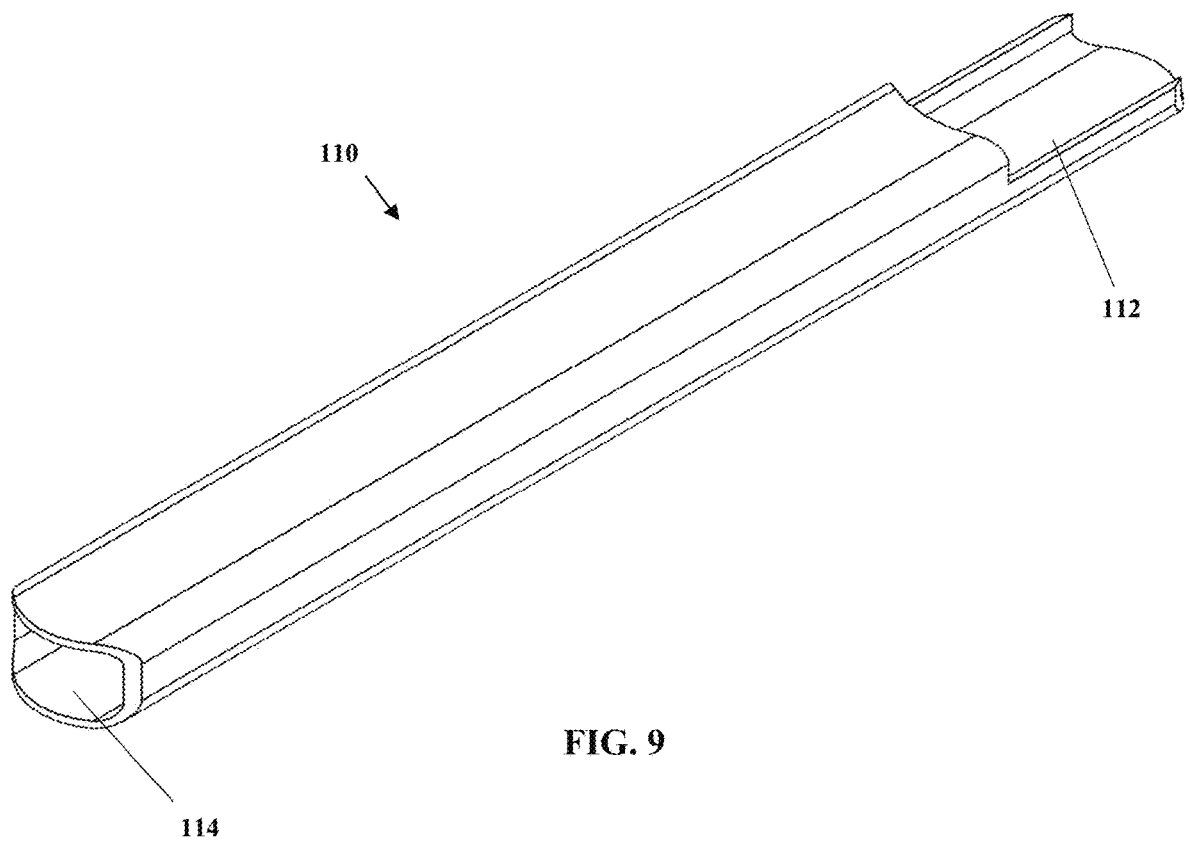
FIG. 9 is a perspective front view of the handle portion.

As shown in FIG. 9, the handle portion 110 includes a longitudinal length with a central handle lumen 112 to house the handle circuit board 150, the bottom housing 140, and the top mount 160. The handle portion 110 includes a top slotted portion 112 to operably couple with the top mount 160 and secure the top mount 160 in the top slotted portion 112. The handle portion 110 includes a bottom lumen portion 114 to secure the bottom housing 140.

Figure 10:
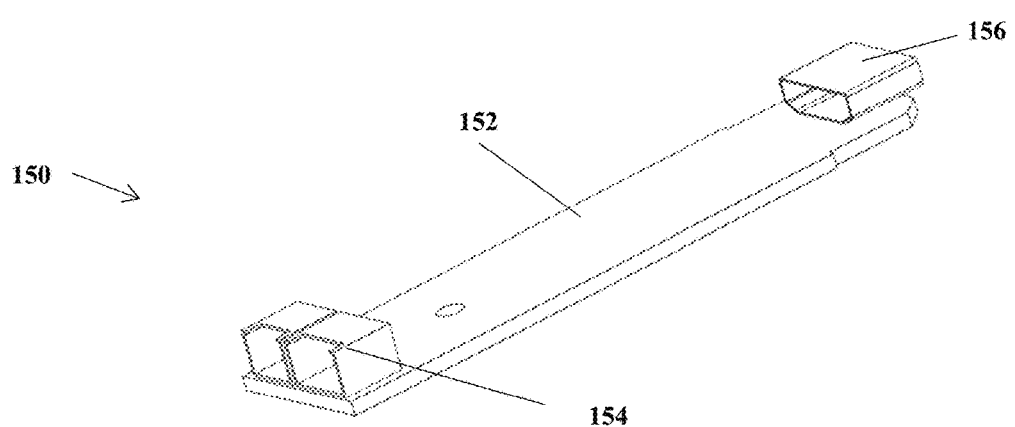
FIG. 10 is a perspective front view of the handle circuit board.
Figure 12A:
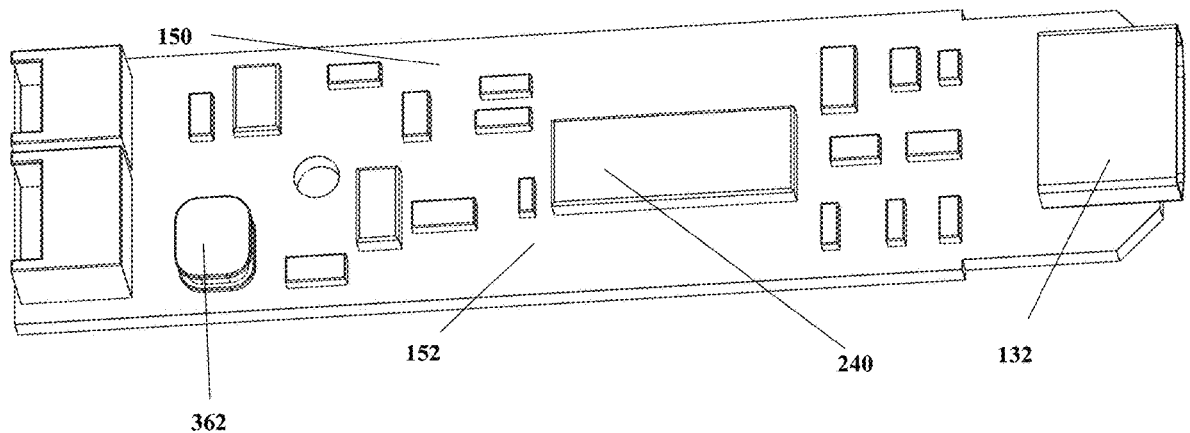
FIG. 12A is a top view of the handle circuit board with the copper foil.
Figure 12B:
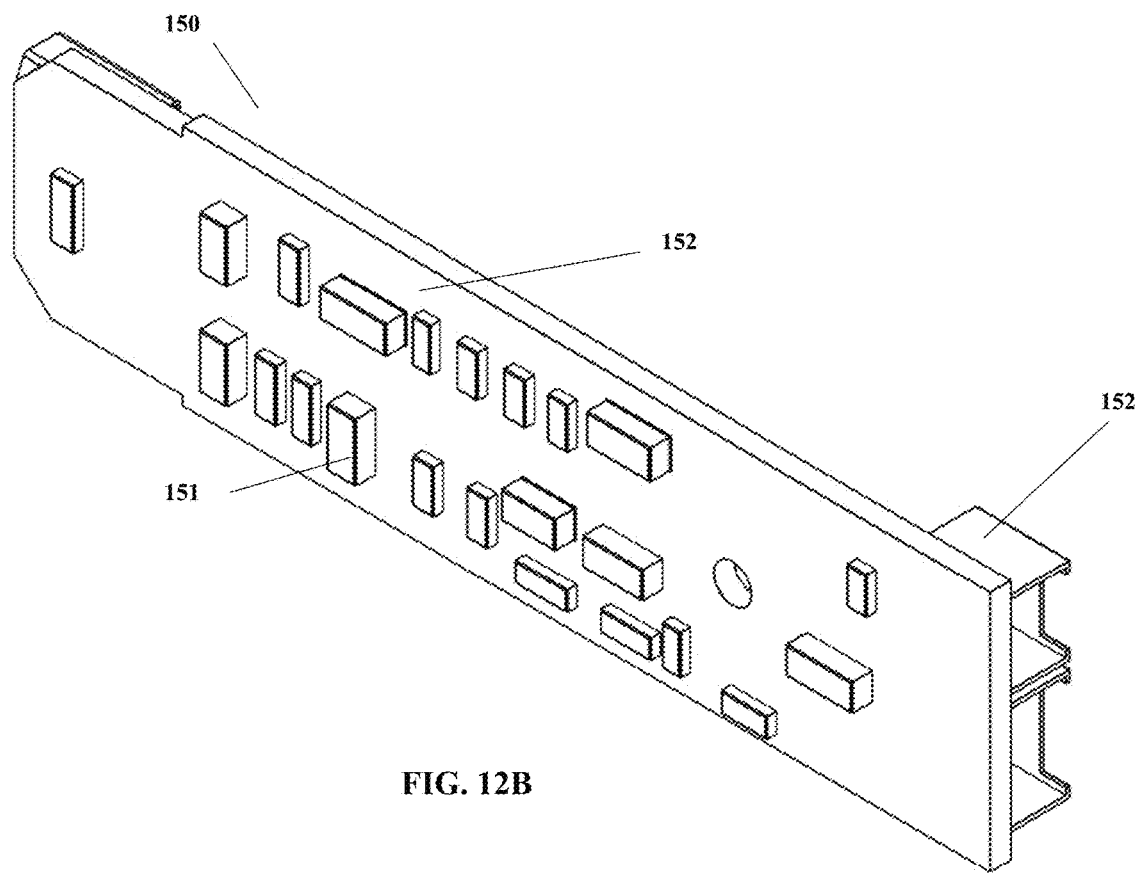
FIG. 12B is a bottom view of the head circuit board.

As shown in FIG. 10, the handle circuit board 150 comprises a printed circuit board 152, a distal connector 154 and a proximal connector 156. The distal connector 154 includes couplings to connect to a power source. The proximal connector 156 includes electrical couplings to connect to the head circuit board 200. The printed circuit board 152 is shown in FIGS. 12A-12B. The handle circuit board 150 includes a bottom portion 158 for the printed circuit board 152. As shown in FIG. 12A, a copper foil 240 is operably coupled with the printed circuit board 152 and transfers the return of the microcurrent generator 362 to the metallic case of the handle portion 110.

Figure 11A:
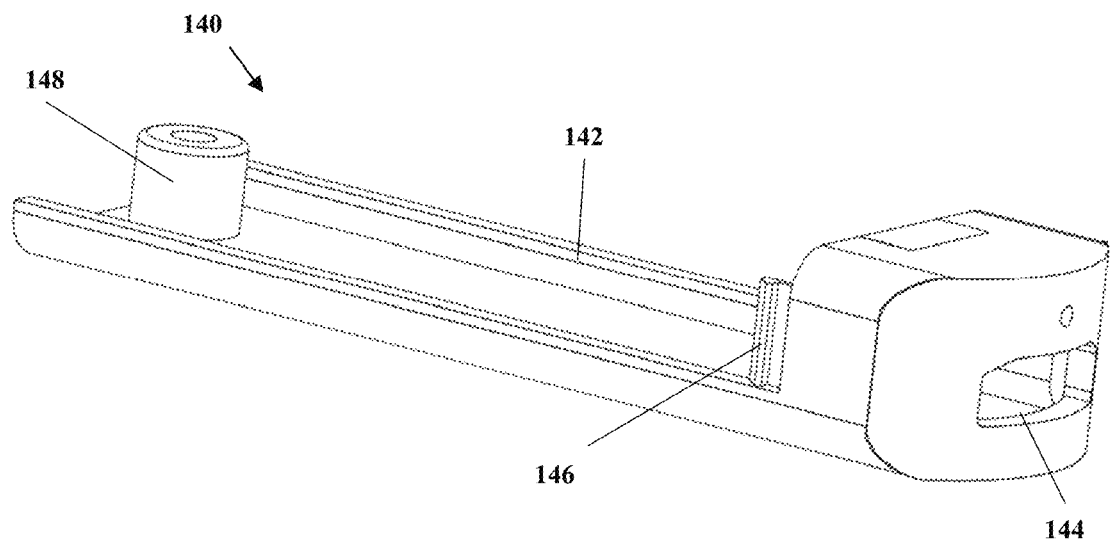
FIG. 11A is a perspective top view of the bottom housing.
Figure 11B:
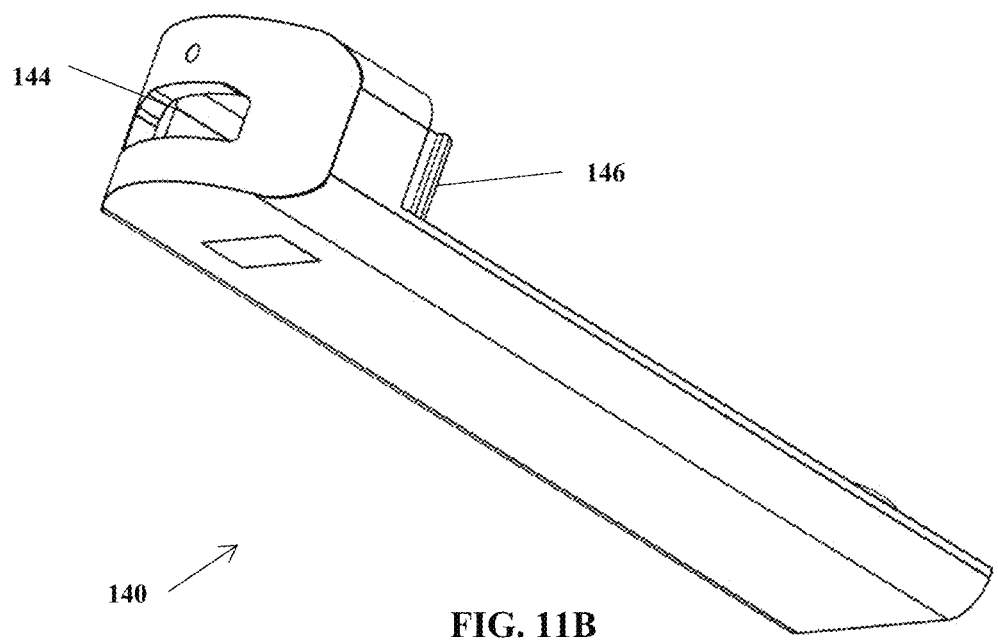
FIG. 11B is a perspective bottom view of the bottom housing.

As shown in FIGS. 11A-11B, the bottom housing 140 comprises a central slide region 142, a distal opening 144, at least two clips 146, and a seated lip 148. The central slide region 142 includes a slotted feature to slide and engage with the handle portion 110. The at least two clips 146 clip and lock into the handle portion 110. The distal opening 144 allows the handle portion 110 to be coupled to an external charging cable or source. The seated lip 148 joins or engages the handle portion 110.

In one embodiment, the vibration motor 350 is attached to the bottom side of the head circuit board 200 and seated within the head housing 230. The handle portion 110 of the device contains the power source 130 and the handle circuit board 150 that contains a micro current generator 362, a battery charging circuit 132, and an impedance power switch function 151. The micro-current system produces an AC current between about 100 μA and about 600 μA and at 8.3 Hz or 10 Hz, according one embodiment. The direct current is pulsed at a frequency between about 0.1 and about 680 Hz with a current range between about 300 and about 600 μA for skin toning and softening fine lines and facial microlifting as described below. The microcurrent includes at least two points of contact on the skin and area in between these two contact points is trained with microcurrent, resulting in wrinkle reduction. In one embodiment, the frequency includes a first frequency at first time period and a second frequency at a second time period, wherein the first frequency and the second frequency is between about 0.1 Hz and 680 Hz. In another embodiment, the signal includes 10 positive pulses and 10 negative pulses following the 10 positive pulses with a frequency at 8.3 pulses per second. In one embodiment, one cycle is a total of 20 pulses, which would take about 2.4 seconds. The maximum current is about 308 μA @ about 500Ω and the maximum voltage is about 28V, according to one embodiment. In another embodiment, the signal includes between about 2 and about 20 positive pulses and the signal includes between about 2 and about 20 negative pulses following the between about 2 and about 20 positive pulses positive pulses with a frequency at 2 and 20 pulses per second.

Figure 13A:
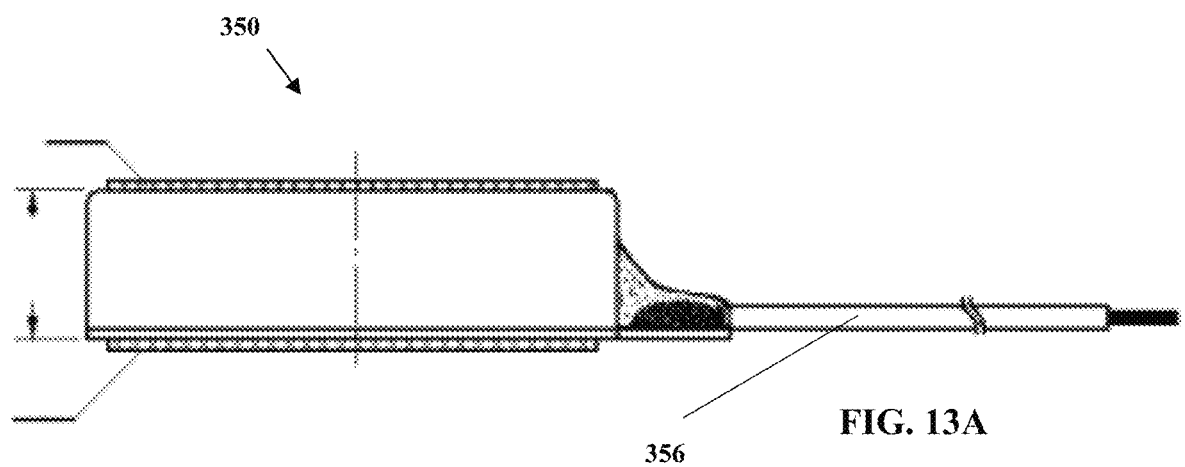
FIG. 13A is a side view of the vibrating motor.
Figure 13B:
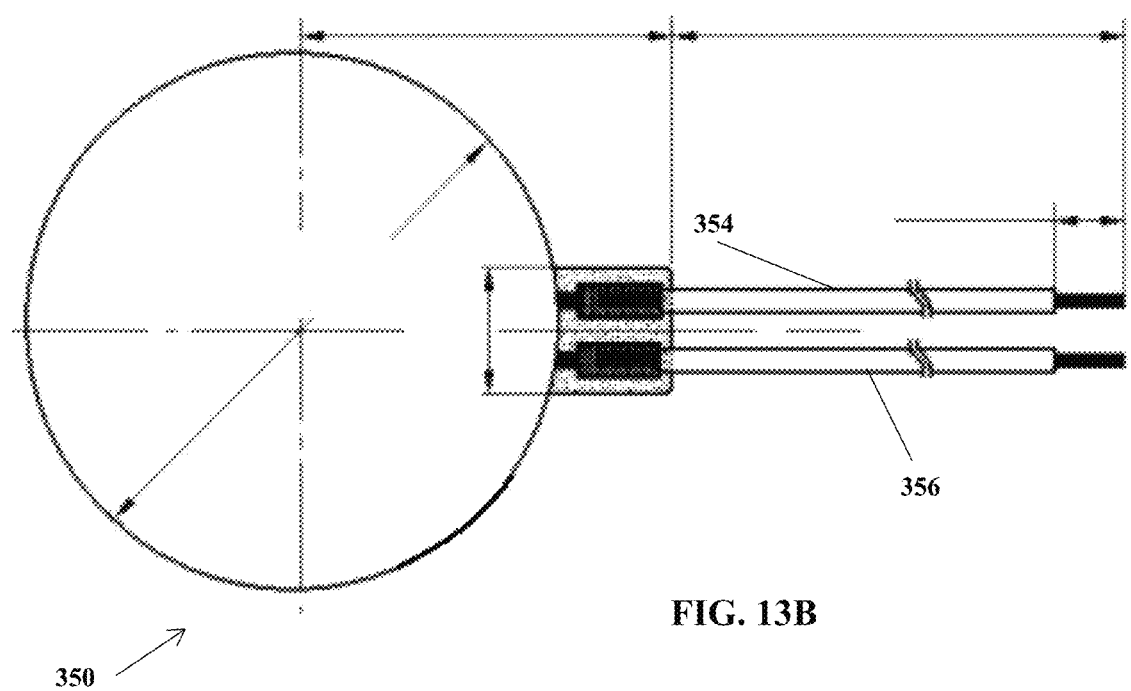
FIG. 13B is a top/bottom view of the vibrating motor.

As shown in FIGS. 13A-13B, the motor 350 includes two electrical couplings 354 and 356. The vibration motor vibrates at a rate between about 200 and about 30000 microvibrations per minute, according to one embodiment. Vibration helps promote blood circulation, which reduces the appearance of dull skin within at least one hour or at least one day after application. It can help visibly reduce the appearance of dark circles and redness after at least hour of treatment or after at least one day of treatment. Application periods for rejuvenating the skin can range from one day to about 3 weeks, from about 1 time a day to about 5 times per day.

Figure 14A:
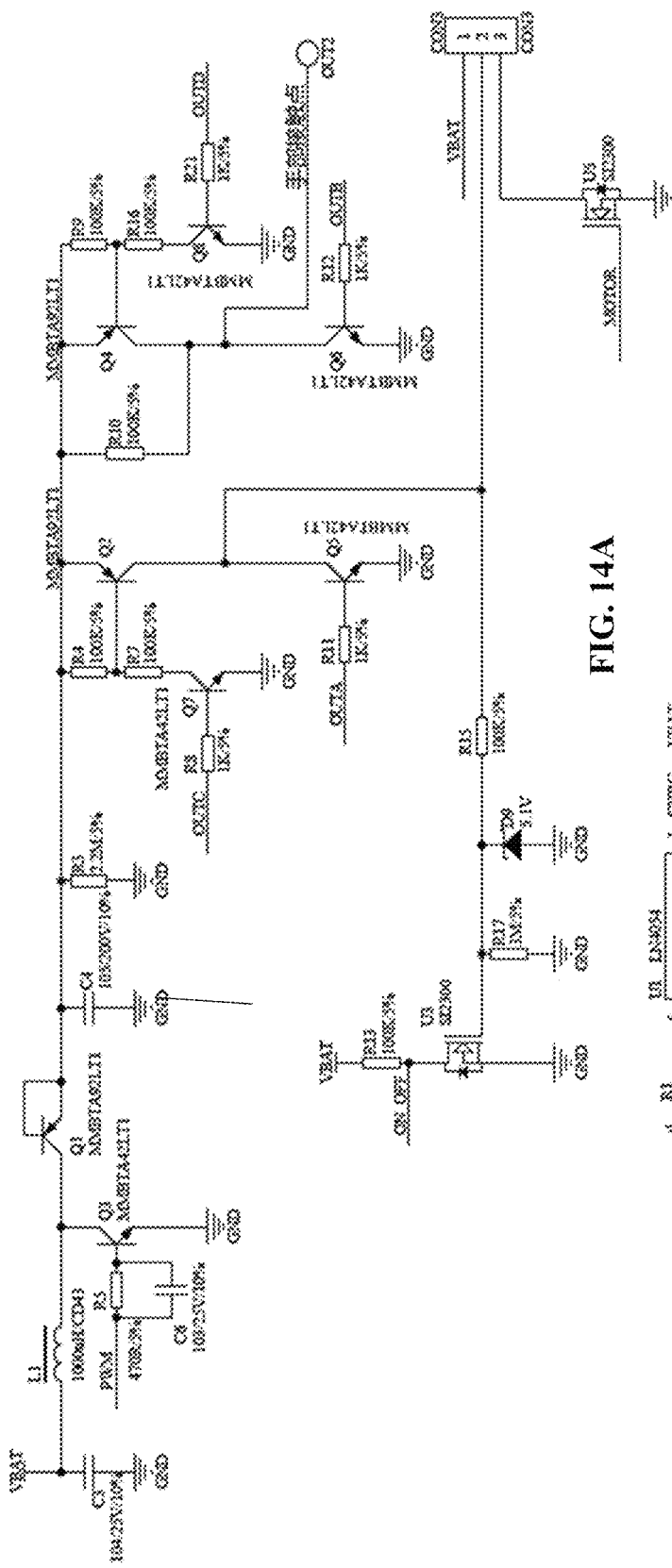
FIGS. 14A-14C are schematic diagrams of the handle circuit board, the head circuit board, and the smart touch circuit.
Figure 14B:
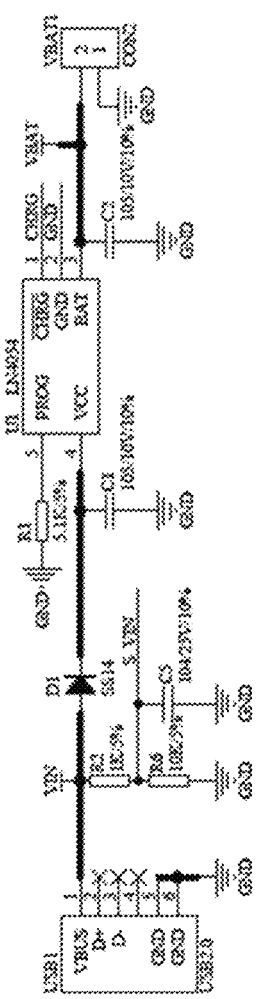
Figure 14C:
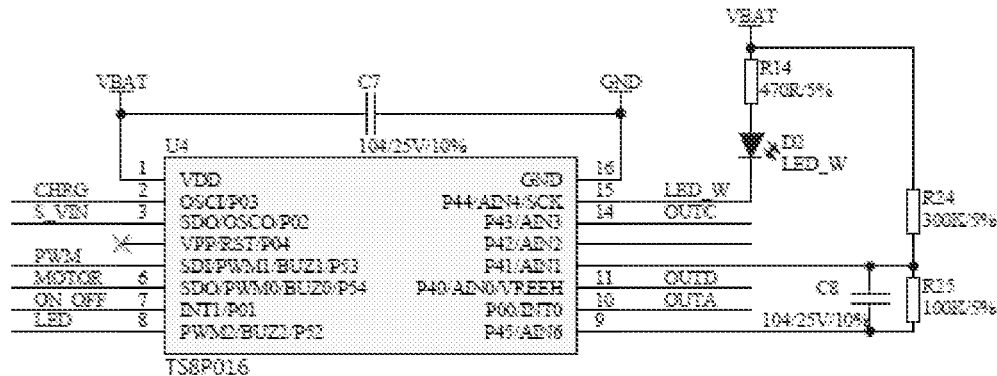

FIGS. 14A-14C are schematic diagrams of the handle circuit board, the head circuit board, and the smart touch circuit. The handle circuit board and the head circuit board are printed circuit boards (PCB), which is a laminated sandwich structure of conductive and insulating layers. PCBs affix electronic components in designated locations on the outer layers by means of soldering and PCBs provide reliable electrical connections (and also reliable open circuits) between the component's terminals in a controlled manner often referred to as PCB design. FIGS. 14A-14C are schematic diagrams of the handle circuit board, the head circuit board, which consists of component symbols connected by lines. The symbols represent basic passive components such as resistors or capacitors to sophisticated integrated circuits such as microcontrollers and on/off switches, and the lines represent conductive pathways that allow electrical current to flow freely from one portion of the circuit to another.

Figure 15A:
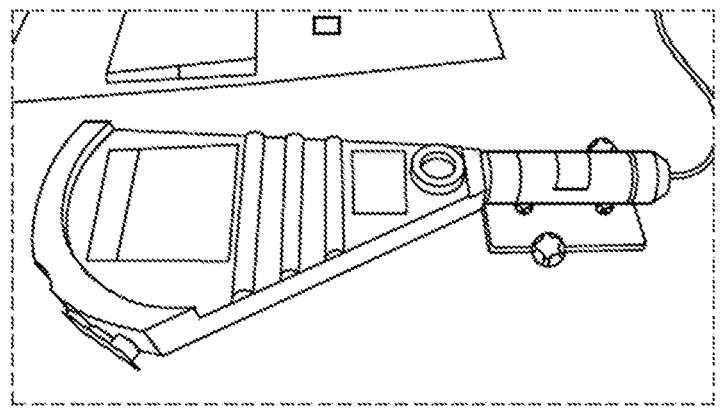
FIG. 15A is a Diffraction Grating Spectrometer for Optical Spectral Analysis.

Optical spectral and intensity analysis were performed on the Electronic skin rejuvenating device Wand. The Electronic skin rejuvenating device comprises a plurality of LED's installed in the center of the head circuit board 190, as shown in FIG. 3A. In one embodiment, all of the LED's are turned on and they stay on as long as the user is holding the handle portion. In one embodiment a minimum of about 5 LED's are included, alternatively, between about 4 and about 50 LED's are included in the head portion. Optical Spectral Analysis was achieved by using a Diffraction Grating Spectrometer, as shown in FIG. 15A, with a digital USB camera at mounted at the viewport. The optical wavelength of the Electronic skin rejuvenating device measures about 660 nm (peak wavelength) and/or 415 nm (peak wavelength) in the Blue Light Wavelength.

Figure 15B:
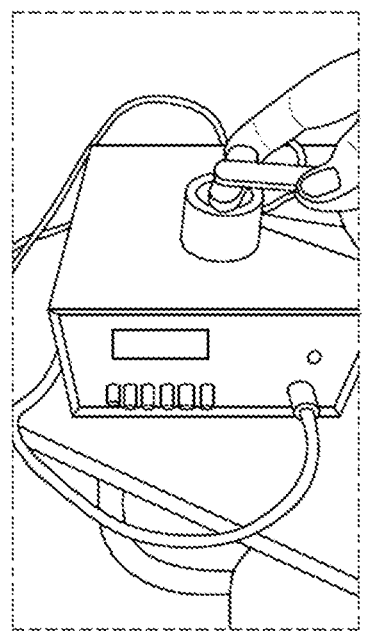
FIG. 15B is a Newport 818-SL silicon optical sensor and associated Model 815 display meter.

The broad fuzzy appearance of the light sampled from the two units is due to the fact that the LED's do not emit coherent light and therefore are slightly broad banded. The intensity of the optical energy from both samples was measure using a calibrated Newport 818-SL silicon optical sensor and associated Model 815 display meter 310, as shown in FIG. 15B. Using the calibration data in the manual for the sensor and wavelength being measured, the measurement of the optical power being emitted from the head portion is about 0.4 uW or microwatts. The optical power enables the red light to penetrate the skin at least 0.1 mm.

As shown in FIG. 3A, the head portion 120 comprises a plurality of mount resistors 340 that are operable within the warming system 340. In one embodiment, the plurality of surface mount resistors are about 750 ohm and about ½ watt, and include between about 1 and about 5 surface mount resistors. The surface mount resistors 340 mounted on the head circuit board 200, which may be a printed circuit board (PCB), and one surface mount resistor 340 is mounted in each corner of the head circuit board 200. Each surface mount resistor is separated by a distance of at least about 2 mm, at least about 3 mm, or at least about 5 mm. The four surface mount resistors deliver a Therapeutic Heat that is between about 38° C. to about 42° C. or between about 95 degrees Fahrenheit and about 110 degrees Fahrenheit. By placing the head portion against the skin, the skin absorbs much of the heat generated by the surface mount resistors and the Therapeutic Heat settles to about 100 degrees. Therapeutic Heat promotes local blood circulation or vasodilation, which helps improve the appearance of the skin, and help topical skincare products be delivered more efficiently into the skin.

The Electronic skin rejuvenating device provides Microcurrent Electrical Neuromuscular Stimulation in a synergistic fashion with the light therapy system 330, the warming system 340, the vibrating massage system 350, and the microcurrent therapy system 360. The synergy applies to the skin therapy treatment, since the combination of the light therapy system 330, the warming system 340, the vibrating massage system 350, and the microcurrent therapy system 160 are greater than the sum of delivering each system to the skin for treatment of a condition. The Electronic skin rejuvenating device design provide levels of Micro-current Electrical Neuromuscular Stimulation under the right conditions. Microcurrent system comprises a much smaller form factor than other prior art devices. The form factor is about 50% smaller than other prior art devices. The operating mode of the Electronic skin rejuvenating device includes a range of energy and a range of current per setting and optionally including a button that increases intensity levels.

The Electronic skin rejuvenating device provides a Microcurrent Electrical Neuromuscular Stimulation dependent or independent on the user. The Electronic skin rejuvenating device supports the delivery of microcurrent despite apparent anodization of the metal case. Using a Tektronix Oscilloscope and probe, the Electronic skin rejuvenating device was forced to turn on by touching the handle and head at the same time. Using binder clips, an oscilloscope probe was connected to the head and the handle and that measurement was captured in FIG. 16.

As shown in FIG. 16, the Electronic skin rejuvenating device emits an irregular square wave at an unloaded amplitude of about 47.2 volts peak 320 to peak 320. In one embodiment, the waveform is selected from the group consisting of: Sawtooth, Reverse sawtooth, Perfect sine wave, and Triangle wave. These waveforms will not be constant and will increase and decrease depending on the wave. This alternating waveform reduces the sensation some may get running microcurrent on high intensities. These waveforms cause no shock, but a gentler increase of the current, which leads to a better experience for the patient. Switching the oscilloscope to the DC mode, the waveform produced continued to be AC in nature indicating the waveform is AC capacitively coupled from the generating electronics, which is a safe DC user exposure parameter for the user.

In one embodiment, a long positive pulse on the head portion attract all the negative ion dirt clutter on patients face. The patient then cleans their face or wipes the dirt. The patient then applies a serum to their face which contains positive ions. The Electronic skin rejuvenating device would then be placed on the face again and produces a long negative pulse, pushing these negative ions in the skin. The average impedance or resistance of the tissue pathway from a handheld instrument to the surface of the head portion can vary. In one embodiment, the average impedance or resistance of the tissue pathway from a handheld instrument to the surface of the head may be in the many hundreds of thousands of ohms to megohms.

A person whose body moisture content is very low, may not receive a relative amount of useful current to the underlying derma. Therefore, in one embodiment, the user uses a conductive serum or gel in conjunction with the wand to benefit from the microcurrent stimulation. A minimum conductive serum includes a base of at least between about 0.1% and 5% aloe vera base.

In another embodiment, if the users' skin and body conform to the well hydrated, low resistance (Moist skin) condition, the Electronic skin rejuvenating device administers a minimum 300 µA of AC current at about 10 Hz. The microcurrent can penetrate the skin at least 0.1 mm. A baseline skin hydration includes measurement by a skin moisture analyzer. Skin moisture analyzers are portable devices that can test various skin factors using something called bioelectric impedance analysis (BIA). Two probes on the end of these small, stick-like gadgets use BIA technology to pass a painless electric current from one sensor through the skin to another.

The method of using the Electronic skin rejuvenating device comprises applying the microcurrent of about 300 µA or more as to increase the amount of ATP (adenosine triphosphate) within the cells of a muscle. The method of applying the microcurrent of 300 µA or more to the skin and underlying muscle of a subject causes an increase in mitochondria and protein synthesis in the muscle, an increase in aminoisobutyric acid uptake, an increase in protein synthesis and Gluconeogenesis (biosynthesis of new glucose) and a 300-500% increase in ATP (Adenosine triphosphate) levels. These dramatic increases in cellular ATP levels have been shown to help muscles retain a re-educated form for longer periods of time and provide muscle toning treatments for the skin. However, for these benefits to be appreciable it is necessary to for the muscle to be manipulated (for example by extending or compressing the muscle) whilst the microcurrent treatment is taking place. A minimum pressure of at least about 0.1 and about 10.0 PSI may be applied. The method of using the Electronic skin rejuvenating device further comprises applying a vibrating massage system to manipulate the skin and muscle so that the muscle is forced into a desired form for re-education. Vibrating Massage system includes vibration energy, which offers a massage to the skin and helps rejuvenate skin and promote local blood circulation.

The method of using the Electronic skin rejuvenating device comprises applying a red light therapy to treat the skin. Red light boosts the energy of the skin cells, allowing the skin cells to work harder and faster on regenerating and healing. One study found that 89% of patients who underwent red light procedures reported significant improvements in facial scarring and marks after one treatment session. The method of using the Electronic skin rejuvenating device comprises using red light with a wavelength of 660 nm to repair damaged skin cells, soften the appearance of wrinkles and scars, and provide an overall radiance to the skin. The method comprises improving a skin complexion and building collagen in the skin. The reduction in wrinkles may be between about 5% when compared to a before and after treatment and 30% when compared to after $1^{st}$ treatment and one month later.). Micro current can also assist in the reduction of facial wrinkles.

The method of using the Electronic skin rejuvenating device comprises applying a heat treatment to the skin to decrease inflammation and encourage vasodilation in the skin. The effects of vasodilation, or the "widening of blood vessels," to improve blood flow and circulation, relieve pain, and decrease infection clogs around the eye area to alleviate dryness and redness. The method comprises using a heated ceramic head to reduce the appearance of dark circles and to flush the skin, according to one embodiment. In another embodiment, the head includes a material made from metal, polymer, ceramic, or a combination thereof.

The method of using the Electronic skin rejuvenating device comprises applying a low vibration treatment to massage the surface of the skin, and increase the moisture content and moisture retention in the skin. The method of applying the low vibration treatment can alleviate pain during a medical procedures and increase skin blood flow after a period of at least one minute. The vibration treatment includes a frequency of between about 10 Hz and about 50 Hz, and a peak acceleration between about 0.1 g and about 0.9 g.

The method of the applying the Electronic skin rejuvenating device to the skin comprises an application time optionally between about 1 minute and about 15 minutes. Optionally, an application time is from about 1 to about 5 minutes, about 2 minutes and about 4 minutes, optionally 3 minutes. It has been found that an application time of three minutes at least twice a week produces excellent results in rejuvenated skin.

Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

The Electronic skin rejuvenating device apparatus as applied to the skin and face of a subject aged 41 years old is shown in FIGS. 17A-17C. The subject had wrinkles and damaged skin 500 as shown in FIG. 17A. After treatment of the skin and face with the Electronic skin rejuvenating device apparatus, the subject skin and face improved with less wrinkles 510, as shown in FIGS. 17B-17C, after 2 weeks and 4 weeks of treatment by the Electronic skin rejuvenating device apparatus, respectively. The treated subject experienced significantly improved skin complexion and skin feeling.

Figure 18A:
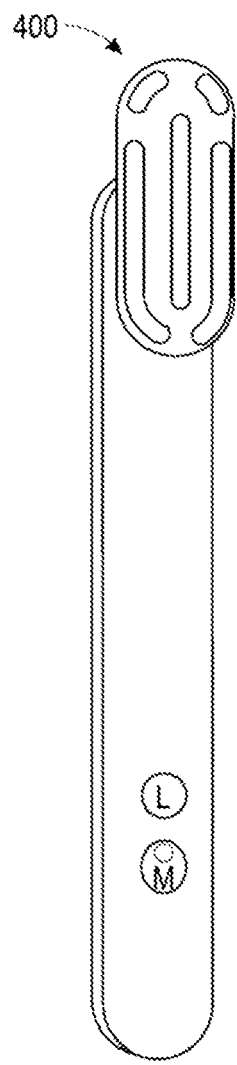
FIGS. 18A-18C are photographs of an alternative embodiment of the Electronic skin rejuvenating device apparatus 400.
Figure 18B:
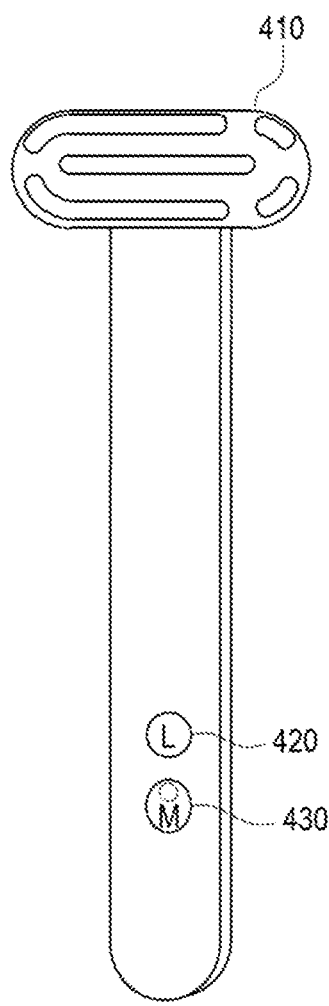
Figure 18C:
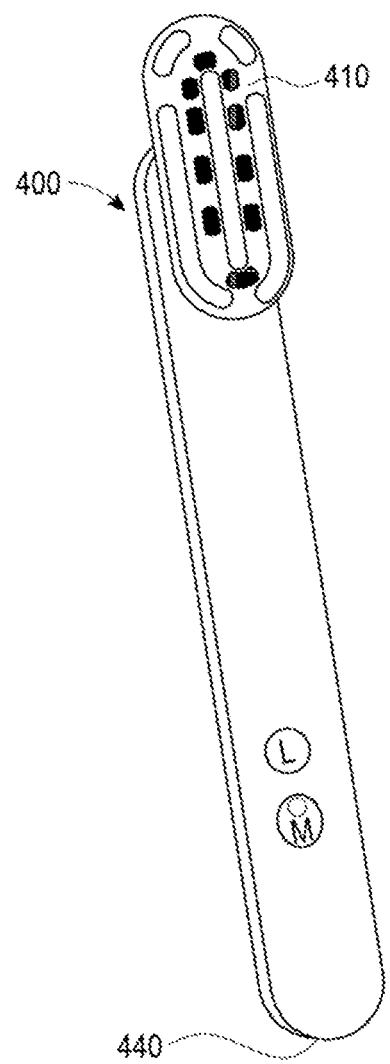

An alternative embodiment of the Electronic skin rejuvenating device apparatus 400 is shown in FIGS. 18A-18B. The Electronic skin rejuvenating device apparatus 400 includes a rotatable head portion 410, where the head 410 can rotate 90° in one direction. Alternatively, the head portion is in a fixed position with respect to the handle. The rotatable head portion 410 includes a radiofrequency emitting mechanism, as shown in FIG. 18C. As shown in FIG. 18B, the Electronic skin rejuvenating device apparatus 400 includes a power switch 430 and a level operation button 420 to modify the level and intensity of the heating system, the vibration mechanism, the microcurrent mechanism, the radiofrequency mechanism, and the light therapy mechanism. As shown in FIG. 18B, the Electronic skin rejuvenating device apparatus 400 includes a charging port 440 to charge the apparatus with a power source charging cable, such as a USB-C or micro-USB port. The Electronic skin rejuvenating device apparatus 400 includes the micro current system can be switched on and off and adjust in strength between level 1, 2 or 3. The head portion 410 is configured with 16 led lights and heating conductor element. The 16 LED lights are divided in two parallel paths. Each path contains 1 resistor (62 Ohm) to limit the current and 8 LEDs, which are also all in parallel. Light output is between about 0.25 mw/cm$^2$ and about 0.53 mw/cm$^2$ at the 660 nm wavelength. The Electronic skin rejuvenating device apparatus includes a 100K radiofrequency (RF), Red/blue light, EMS, warm, vibration. The microcurrent mechanism includes a microcurrent of about 400 microampere (uA) and a voltage of about 31.74V with two resistors. The microcurrent is transferred using spring connectors (left side 3×) and a conducting mesh (right side 2×). The vibration mechanism vibrates 1 time per minute, or vibrates 2 times every 5 minutes, then loops to repeat. The heating system is created by 6 resistors at about 10 k Ohm and transfers the heat to the metal bars on the outside of the treatment head.

Figure 19:
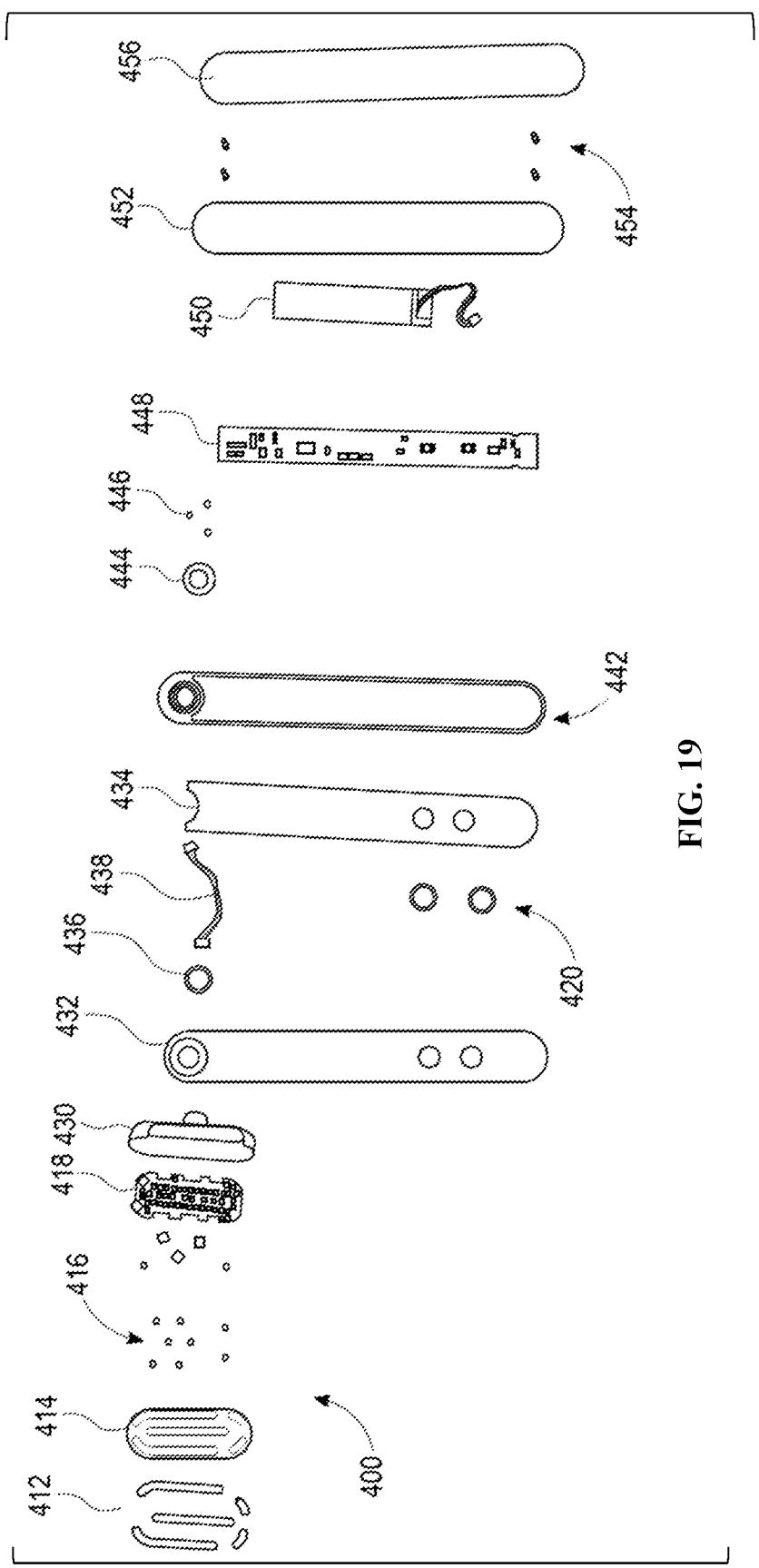
FIG. 19 is an exploded view of the Electronic skin rejuvenating device apparatus 400, according to one embodiment.

As show in FIG. 19, the Electronic skin rejuvenating device apparatus 400 includes a probe of the head 412, a front cover head 414, a plurality of fasteners 416, a PCBA light control board 418, a rear cover of the head 430, a front body cover 432, a rear body cover 434, an O-ring seal 436, a cable 438, a body frame 442, a metal plate rotational constraint 444, a plurality of fasteners 446, a PCBA main board 448, the buttons 420, a power source 450, an Inner back plate 452, a plurality of fasteners 454, and a Back cover 456. The PCB main board 448 includes the 100K RF, Red/blue light, EMS, warm, vibration systems. The PCBA light control board 418 is configured with 18 LED lights and the heating conductor element.

Figure 20A:
FIGS. 20A-20B are photographs of a subject before Electronic skin rejuvenating device treatment, showing the subject had wrinkles and damaged skin; and after treatment of the skin and face with the Electronic skin rejuvenating device apparatus, the subject skin and face improved, as shown in FIGS. 20C-20D, after 2 weeks of treatment by the Electronic skin rejuvenating device apparatus.
Figure 20B:
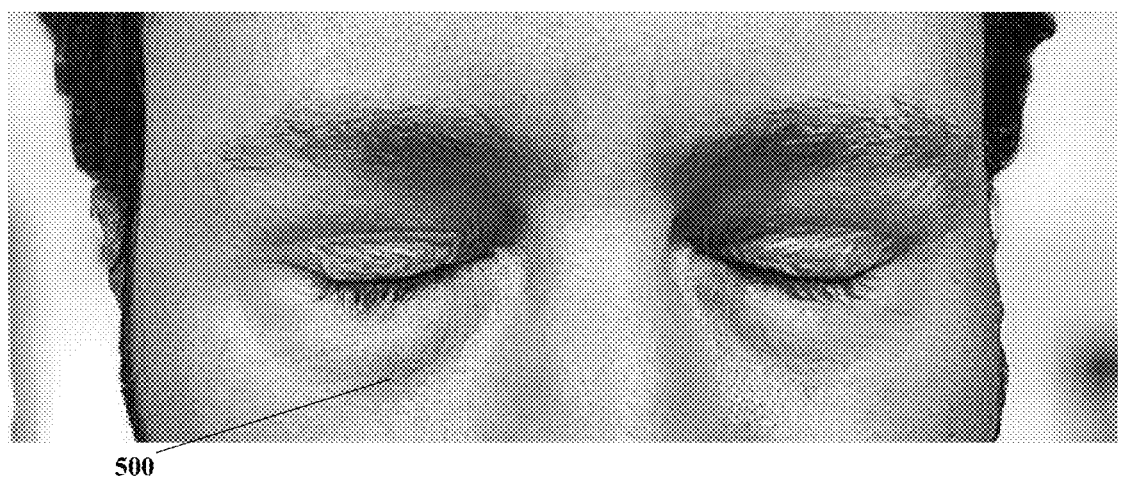
Figure 20C:
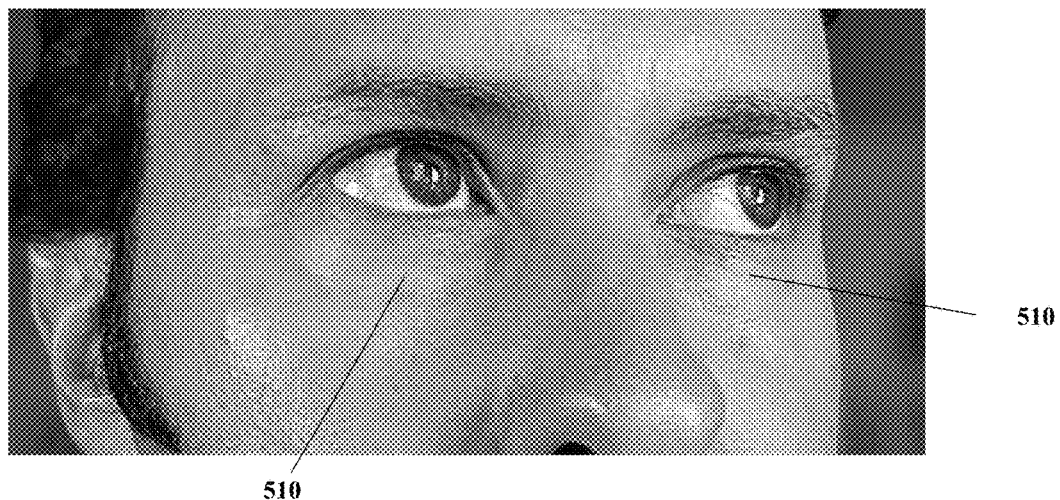
Figure 20D:

The Electronic skin rejuvenating device apparatus as applied to the skin and face of a subject aged is shown in FIGS. 20A-20D. The subject had wrinkles and damaged skin 500 as shown in FIG. 20A-20B. After treatment of the skin and face with the Electronic skin rejuvenating device apparatus, the subject skin and face improved with less wrinkles 510, as shown in FIGS. 20C-20D, after 2 weeks of treatment by the Electronic skin rejuvenating device apparatus, respectively.

Figure 21A:
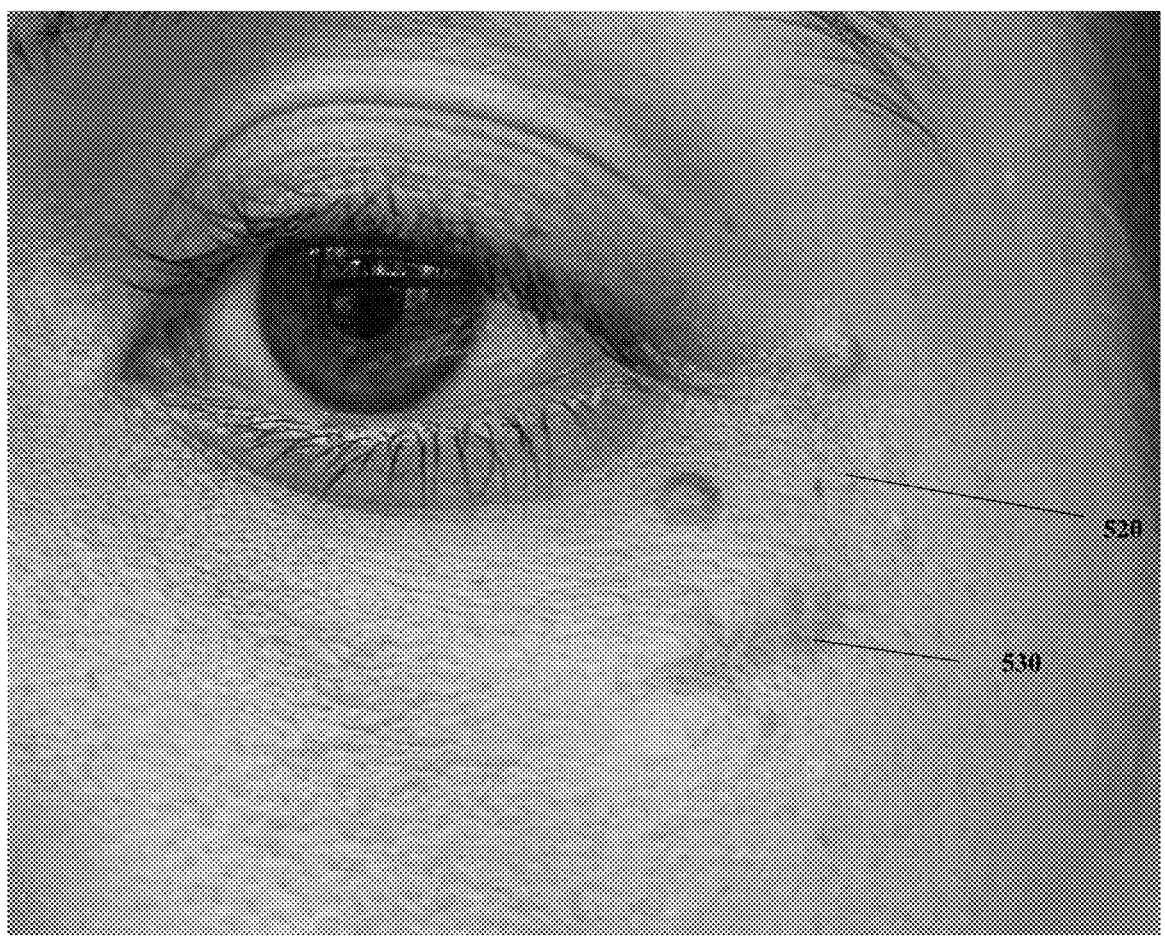
FIG. 21A is a photograph of a subject before Electronic skin rejuvenating device treatment, showing the subject had redness in the skin and a scar; and after treatment of the skin and face with the Electronic skin rejuvenating device apparatus, the subject skin cleared and the scar was healed, as shown in FIG. 21B, after 2 weeks of treatment by the Electronic skin rejuvenating device apparatus.
Figure 21B:

FIG. 21A is a photograph of a subject before Electronic skin rejuvenating device treatment, showing the subject had redness in the skin 520 and a scar 530; and after treatment of the skin and face with the Electronic skin rejuvenating device apparatus, the subject skin cleared 540 and the scar was healed 550, as shown in FIG. 21B, after 2 weeks of treatment by the Electronic skin rejuvenating device apparatus.

Embodiments of the invention were described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the treatment area of the subject.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. An Electronic skin rejuvenating apparatus to treat skin conditions comprising:
    a handle portion and a head portion, wherein the head portion is operably coupled with the handle portion;
    the handle portion comprises a power source, a bottom housing, a handle circuit board, a top mount, and a back ring;
    the head portion comprises a cover, a head cover, a head circuit board, a vibration motor, a head housing, wherein the power source is operably coupled with the handle circuit board and the head circuit board;
    the head circuit board comprises a light therapy system, a warming system, a vibrating massage system, and a microcurrent therapy system, wherein the light therapy system comprises a plurality of light emitting sources that emit a therapeutic light, including a red light between about 630 nm to about 670 nm to penetrate the skin at least 0.1 mm or a blue light between about 410 nm to about 465 nm to penetrate the skin;
    the warming system includes a heating element to warm the skin between about 93 and about 110 degrees Fahrenheit to promote local blood circulation or vasodilation;
    the vibrating massage system comprises the vibration motor to vibrate the head portion against the skin, the motor vibrates at a rate of between about 300 and about 30000 microvibrations per minute;
    the microcurrent therapy system produces at least a 300 µA of AC current at about 10 Hz and produces a direct current that is pulsed at a frequency between about 0.1 and about 680 Hz with a current range between about 100-600 µA for skin toning, softening fine lines and facial microlifting;
    wherein the light therapy system, the warming system, the vibrating massage system, and the microcurrent therapy system employ heat, light, vibration and microcurrent electrical neuromuscular stimulation of the skin to treat eye and facial skin conditions;
    wherein the plurality of light emitting sources are light-emitting diodes; the handle portion does not include any buttons to operate; the head portion comprises a touch activation sensor that turns the Electronic skin rejuvenating apparatus on when the touch activation sensor uses an impedance activation scheme of about 13 megohms or less; and the microcurrent therapy system stimulates the local muscles in the skin and;
    the head housing comprises a mounted seat for the head circuit board to be secured there within; the head housing comprises at least two seated pins to secure the head circuit board, whereby the seated pins coaxially couple through the at least two holes on the exterior flanges of the head circuit board; the head housing comprises a central lumen portion, whereby the head housing is rotatable about a central axis of the central lumen portion; the central lumen portion includes a triangular seat on the exterior surface of the head housing; wherein the triangular seat allows the head housing to rotate to a fixed position, such that the head housing rotates to a right angle with respect to the handle portion; and the head housing comprises at least four seated columns by which the head housing is secured to the head cover.

2. The apparatus of claim 1, wherein the head portion includes a spring loaded pogo pin that presses on the inside of the head cover of the head portion to transfer the other pole of a microcurrent generator to the head portion of the Electronic skin rejuvenating apparatus; wherein the micro current is configured to be delivered to the head portion of the apparatus using the body of the handle portion as the return connection; the micro current is configured to flow through the users' hand and body and the circuit is completed at the interface of the Electronic skin rejuvenating apparatus' head portion and the skin it is applied to.

3. The apparatus of claim 2, wherein the head cover includes generally curvilinear configuration shaped to fit over the head housing; the head cover comprises a central window portion sized to permit the light therapy system from the head housing to transmit optical energy through the central window; the cover fits over the central window portion; the cover comprises a seated portion to fit within over the central window portion of the head housing; the head cover comprises a cover lumen portion that fits over the exterior and circumference of the head housing; the four seated columns are joined to the cover lumen portion; the material of the head cover permits the micro current system to transmit microcurrent there through to the user's skin.

4. The apparatus of claim 3, wherein the top mount includes a top circular portion and a bottom slotted portion; the bottom slotted portion is secured with the handle portion; the top mount comprises a circular seat on the back portion to further secure the top mount to the handle portion; the top circular portion rotatably couples with the head housing and the central lumen and the triangular seat; the head housing is secured and rotatably coupled to the top mount by way of the back ring; and the top circular portion includes a slotted circular seat in which to secure the back ring.

5. The apparatus of claim 4, wherein the back ring includes a central triangular portion that operably couples with the head housing and the triangular seat; the back ring includes an outer stop portion, which stops the rotation of the head housing to be at a right angle with respect to the handle portion.

6. The apparatus of claim 5, wherein the handle portion includes a longitudinal length with a central handle lumen to house the handle circuit board, the bottom housing, and the top mount; The handle portion includes a top slotted portion to operably couple with the top mount and secure the top mount in the top slotted portion; the handle portion includes a bottom lumen portion to secure the bottom housing.

7. The apparatus of claim 6, wherein the handle circuit board comprises a printed circuit board, a distal connector and a proximal connector; the distal connector includes couplings to connect to the power source; the proximal connector includes electrical couplings to connect to the head circuit board; a copper foil is operably coupled with the printed circuit board and transfers the return of the microcurrent generator to a metallic case of the handle portion.

8. The apparatus of claim 7, wherein the bottom housing comprises a central slide region, a distal opening, at least two clips, and a seated lip; the central slide region includes a slotted feature to slide and engage with the handle portion; the at least two clips clip and lock into the handle portion; the distal opening allows the handle portion to be coupled to an external charging cable or source; and the seated lip joins the handle portion.

9. The apparatus of claim 8, wherein the micro-current therapy system produces about 300 uA of AC current at about 10 Hz; the direct current is pulsed at a frequency between about 0.1 and about 680 Hz with a current range between about 300-500 µA for skin toning and softening fine lines and facial microlifting.

10. The apparatus of claim 9, wherein the warming system comprises a plurality of surface mount resistors that are operable at about 750 ohm and about ½ watt of power; wherein the surface mount resistors are mounted on the head circuit board on each corner of the head circuit board; each surface mount resistor is separated by a distance of at least about 2 mm.

11. An Electronic skin rejuvenating apparatus to treat skin conditions comprising:
a handle portion and a head portion, wherein the head portion is operably coupled with the handle portion;
the handle portion comprises a power source, a bottom housing, a handle circuit board, a top mount, and a back ring;
the head portion comprises a cover, a head cover, a head circuit board, a vibration motor, a head housing, wherein the power source is operably coupled with the handle circuit board and the head circuit board;
the head circuit board comprises a light therapy system, a warming system, a vibrating massage system, and a microcurrent therapy system, wherein the light therapy system comprises a plurality of light emitting sources that emit a therapeutic light, including a red light between about 630 nm to about 670 nm to penetrate the skin at least 0.1 mm or a blue light between about 410 nm to about 465 nm to penetrate the skin;

the warming system includes a heating element to warm the skin between about 93 and about 110 degrees Fahrenheit to promote local blood circulation or vasodilation;
the vibrating massage system comprises the vibration motor to vibrate the head portion against the skin, the motor vibrates at a rate of between about 300 and about 30000 microvibrations per minute;
the microcurrent therapy system produces at least a 300 µA of AC current at about 10 Hz and produces a direct current that is pulsed at a frequency between about 0.1 and about 680 Hz with a current range between about 100-600 µA for skin toning, softening fine lines and facial microlifting;
wherein the light therapy system, the warming system, the vibrating massage system, and the microcurrent therapy system employ heat, light, vibration and microcurrent electrical neuromuscular stimulation of the skin to treat eye and facial skin conditions;
wherein the plurality of light emitting sources are light-emitting diodes; the handle portion includes a button to operate; the head portion comprises a touch activation sensor that turns the Electronic skin rejuvenating apparatus on when the touch activation sensor uses an impedance activation scheme of about 13 megohms or less; and the microcurrent therapy system stimulates the local muscles in the skin;
wherein the head portion includes a spring-loaded element that presses on the inside of the head cover of the head portion to transfer a pole of a microcurrent generator to the head portion;
the head housing comprises a mounted seat for the head circuit board to be secured there within; the head housing comprises at least two seated pins to secure the head circuit board, whereby the seated pins coaxially couple through the at least two holes on the exterior flanges of the head circuit board; the head housing comprises a central lumen portion, whereby the head housing is rotatable about a central axis of the central lumen portion; the central lumen portion includes a triangular seat on the exterior surface of the head housing; wherein the triangular seat allows the head housing to rotate to a fixed position, such that the head housing rotates to a right angle with respect to the handle portion; and the head housing comprises at least four seated columns by which the head housing is secured to the head cover.

12. The apparatus of claim 11, wherein the head cover includes generally curvilinear configuration shaped to fit over the head housing; the head cover comprises a central window portion sized to permit the light therapy system from the head housing to transmit optical energy through the central window; the cover fits over the central window portion; the cover comprises a seated portion to fit within over the central window portion of the head housing; the head cover comprises a cover lumen portion that fits over the exterior and circumference of the head housing; the four seated columns are joined to the cover lumen portion; the material of the head cover permits the micro current therapy system to transmit microcurrent there through to the user's skin.

13. The apparatus of claim 12, wherein the top mount includes a top circular portion and a bottom slotted portion; the bottom slotted portion is secured with the handle portion; the top mount comprises a circular seat on the back portion to further secure the top mount to the handle portion; the top circular portion rotatably couples with the head housing and the central lumen and the triangular seat; the head housing is secured and rotatably coupled to the top mount by way of the back ring; and the top circular portion includes a slotted circular seat in which to secure the back ring.

14. The apparatus of claim 13, wherein the back ring includes a central triangular portion that operably couples with the head housing and the triangular seat; the back ring includes an outer stop portion, which stops the rotation of the head housing to be at a right angle with respect to the handle portion.

15. The apparatus of claim 14, wherein the handle portion includes a longitudinal length with a central handle lumen to house the handle circuit board, the bottom housing, and the top mount; the handle portion includes a top slotted portion to operably couple with the top mount and secure the top mount in the top slotted portion; the handle portion includes a bottom lumen portion to secure the bottom housing.

16. The apparatus of claim 15, wherein the handle circuit board comprises a printed circuit board, a distal connector and a proximal connector; the distal connector includes couplings to connect to the power source; the proximal connector includes electrical couplings to connect to the head circuit board; a copper foil is operably coupled with the printed circuit board and transfers the return of the micro-current generator to a metallic case of the handle portion.

17. The apparatus of claim 16, wherein the bottom housing comprises a central slide region, a distal opening, at least two clips, and a seated lip; the central slide region includes a slotted feature to slide and engage with the handle portion; the at least two clips clip and lock into the handle portion; the distal opening allows the handle portion to be coupled to an external charging cable or source; and the seated lip joins the handle portion.

18. The apparatus of claim 17, wherein the micro-current therapy system produces about 300 µA of AC current at about 10 Hz; the direct current is pulsed at a frequency between about 0.1 and about 680 Hz with a current range between about 300-500 µA for skin toning and softening fine lines and facial microlifting.

19. The apparatus of claim 18, wherein the warming system comprises a plurality of surface mount resistors that are operable at about 750 ohm and about ½ watt of power; wherein the surface mount resistors are mounted on the head circuit board on each corner of the head circuit board; each surface mount resistor is separated by a distance of at least about 2 mm.

* * * * *